(12) United States Patent
Lippmann et al.

(10) Patent No.: US 12,404,496 B2
(45) Date of Patent: Sep. 2, 2025

(54) BIOREACTOR SYSTEMS

(71) Applicant: Vanderbilt University, Nashville, TN (US)

(72) Inventors: Ethan S. Lippmann, Nashville, TN (US); Alejandra I. Romero-Morales, Nashville, TN (US); Brian J. O'Grady, Nashville, TN (US); Kylie M. Balotin, Nashville, TN (US); Leon M. Bellan, Nashville, TN (US); Vivian Gama, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 768 days.

(21) Appl. No.: 17/623,391

(22) PCT Filed: Jun. 28, 2020

(86) PCT No.: PCT/US2020/040026
§ 371 (c)(1),
(2) Date: Dec. 28, 2021

(87) PCT Pub. No.: WO2020/264455
PCT Pub. Date: Dec. 30, 2020

(65) Prior Publication Data
US 2022/0364061 A1 Nov. 17, 2022

Related U.S. Application Data

(60) Provisional application No. 62/868,332, filed on Jun. 28, 2019.

(51) Int. Cl.
  *C12N 5/071* (2010.01)
  *C12M 1/00* (2006.01)
  (Continued)

(52) U.S. Cl.
  CPC .......... *C12N 5/0697* (2013.01); *C12M 23/12* (2013.01); *C12M 27/06* (2013.01); *C12M 41/14* (2013.01); *C12M 41/42* (2013.01)

(58) Field of Classification Search
  None
  See application file for complete search history.

(56) References Cited

U.S. PATENT DOCUMENTS 2,526,351 A    10/1950   Grubelic
5,587,298 A    12/1996   Horigane et al.
(Continued)

OTHER PUBLICATIONS

Anlar et al., "Apoptosis in the developing human brain: A preliminary study of the frontal region", Early Hum. Dev., 2003, vol. 71, pp. 53-60.
(Continued)

*Primary Examiner* — Michael A Marcheschi
*Assistant Examiner* — Ashley Lopezlira
(74) *Attorney, Agent, or Firm* — Michael Best & Friedrich LLP

(57) ABSTRACT

Bioreactor systems can include a first frame and a second frame, a well plate, a motor plate, a motor, and a controller. The first frame may define a well plate inset and standoff insets for a first set of metal standoffs. The second frame may define a plurality of mounts and a plurality of insets for a second set of metal standoffs. A gear may be positioned in each of the plurality of mounts. A paddle may be coupled to each of the gears. The well plate can be positioned within the well plate inset. The motor plate can be supported by and connected to the first set of metal standoffs and the second set of metal standoffs. The motor can be mounted on the motor plate and operatively connected to one of the plurality of gears.

19 Claims, 24 Drawing Sheets

(51) Int. Cl.
  *C12M 1/06* (2006.01)
  *C12M 1/32* (2006.01)
  *C12M 1/34* (2006.01)

(56) References Cited

U.S. PATENT DOCUMENTS

| | | |
|---|---|---|
| 7,604,987 B2 | 10/2009 | Hutmacher et al. |
| 9,550,157 B2 | 1/2017 | Erdenberger et al. |
| 2013/0126436 A1* | 5/2013 | Ok ............................ B03C 1/032 366/342 |
| 2017/0113197 A1* | 4/2017 | Middleton ............ B01F 27/213 |
| 2018/0154321 A1* | 6/2018 | Ozeki ..................... B01F 27/85 |
| 2018/0273898 A1* | 9/2018 | Chen ........................ A61L 27/54 |
| 2018/0334646 A1* | 11/2018 | Song ........................ C12M 21/08 |
| 2019/0062689 A1* | 2/2019 | Ariga ........................ G06T 7/11 |
| 2019/0083974 A1* | 3/2019 | Cambron .............. B01L 3/5025 |

OTHER PUBLICATIONS

Camp et al., "Human cerebral organoids recapitulate gene expression programs of fetal neocortex development", PNAS, 2015, pp. 15672-15677.
Elkabetz et al., "Human ES cell-derived neural rosettes reveal a functionally distinct early neural stem cell stage", Genes Dev., 2008, vol. 22, pp. 152-165.
Frotscher, "Cajal-Retzius cells, Reelin, and the formation of layers", Curr. Opin. Neurobiol., 1998, vol. 8, pp. 570-575.
Gerrard et al., "Differentiation of human embryonic stem cells to neural lineages in adherent culture by blocking bone morphogenetic protein signaling", Stem Cells, 2005, vol. 23, pp. 1234-1241.
Hevner et al., "Tbr1 regulates differentiation of the preplate and layer 6", Neuron., 2001, vol. 29, pp. 353-366.
Hříbková et al., "Calcium signaling mediates five types of cell morphological changes to form neural rosettes", J. Cell Sci., 2018, vol. 131, pp. 1-12.
Kadoshima et al., "Self-organization of axial polarity, inside-out layer pattern, and species-specific progenitor dynamics in human ES cell-derived neocortex", Proc. Natl. Acad. Sci., 2013, vol. 111, No. 20, pp. 20284-20289.
Kelava et al., "Stem Cell Models of Human Brain Development", Cell Stem Cell, 2016, vol. 18, pp. 736-748.
Kriegstein et al., "The Glial Nature of Embryonic and Adult Neural Stem Cells", Annu. Rev. Neurosci., 2009, vol. 32, pp. 149-184.
Kuan et al., "Mechanisms of programmed cell death in the developing brain", Trends Neurosci., 2000, vol. 23, pp. 291-297.
Lancaster et al., "Cerebral organoids model human brain development and microcephaly", Nature, 2013, vol. 501, pp. 373-379.
Lancaster et al., "Generation of cerebral organoids from human pluripotent stem cells", Nat. Protoc., 2014, vol. 9, pp. 2329-2340.
Lancaster et al., "Guided self-organization and cortical plate formation in human brain organoids", Nature Biotechnology, vol. 35, No. 7, 2017, pp. 659-666.
Marton et al., "Differentiation and maturation of oligodendrocytes in human three-dimensional neural cultures", Nat. Neurosci., 2019, vol. 22, pp. 484-491.
Nonomura et al., "Local apoptosis modulates early mammalian brain development through the elimination of morphogen-producing cell", Dev. Cell., 2013, vol. 27, pp. 621-634.
Pasca et al., "Functional cortical neurons and astrocytes from human pluripotent stem cells in 3D culture", Nat Methods., 2015, vol. 12, pp. 671-678.
Pasca et al., "Human 3D cellular model of hypoxic brain injury of prematurity", Nat. Med., 2019, vol. 25, pp. 784-791.
Qian et al., "Brain-Region-Specific Organoids Using Mini-bioreactors for Modeling ZIKV Exposure", Cell, 2016, vol. 165, pp. 1238-1254.
Qian et al., "Generation of human brain region-specific organoids using a miniaturized spinning bioreactor", Nat. Protoc., 2018, vol. 13, pp. 565-580.
Quadrato et al., "Cell diversity and network dynamics in photosensitive human brain organoids", Nature, 2017, vol. 545, pp. 48-53.
Shafit-Zagardo et al., "Making sense of the multiple MAP-2 transcripts and their role in the neuron", Mol. Neurobiol., 1998, vol. 16, pp. 149-162.
Subramanian et al., "Dynamic behaviour of human neuroepithelial cells in the developing forebrain", Nat. Commun., 2017, vol. 8, 14167.
Sutcliffe et al., "A Simple Method of Generating 3D Brain Organoids Using Standard Laboratory Equipment", Humana Press, 2017, pp. 1-12.
White et al., "Qualitative and quantitative estimates of apoptosis from birth to senescence in the rat brain", Cell Death Differ., 2001, vol. 8, pp. 345-356.
Yoon et al., "Reliability of human cortical organoid generation", Nat. Methods., 2019, vol. 16, pp. 75-78.
Zhang et al., "In vitro differentiation of transplantable neural precursors from human embryonic stem cells", Nat. Biotechnol., 2001, vol. 19, pp. 1129-1133.
International Search Report and Written Opinion for Application No. PCT/US20/40026 dated Sep. 28, 2020 (14 pages).
International Preliminary Report on Patentability for Application No. PCT/US2020/040026 dated Dec. 28, 2021 (7 pages).
3Dnamics, "Science! SpinOmega™", <https://web.archive.org/web/20171119001026/https:www.3dnamics.com/technology>, 2017, 12 pages.

* cited by examiner

Day 60 organoids

Day 60 organoids

Day 150 organoids

Cl Caspase-3, Nestin, Nuclei

Cl Caspase-3, CTIP2, CUX1

BIOREACTOR SYSTEMS

CROSS-REFERENCE TO RELATED APPLICATION

The patent application is the U.S. national stage entry, under 35 U.S.C. § 371, of International Application Number PCT/US2020/040026, filed Jun. 28, 2020, which claims the priority benefit of U.S. Provisional Application No. 62/868,332, filed Jun. 28, 2019, the entire contents of each of which are hereby incorporated by reference.

STATEMENT OF GOVERNMENT INTEREST

This invention was made with government support under contract numbers 1R35GM128915-01, 1R21 CA227483-01A1, T32 AG058524, and T32 ES007028, awarded by the U.S. National Institutes of Health (NIH). The government has certain rights in the invention.

INTRODUCTION

Brain organoids are three-dimensional (3D) structures formed from neural stem cells (NSCs) derived from human pluripotent stem cells (hPSCs) that can effectively model human brain development up to 12-14 weeks post-conception, a time period which includes critical patterning events in the cerebral cortex and other brain regions. On a cellular level, brain organoids show a high level of similarity to the in vivo developing human brain in the early stages of development, including progenitor zones (ventricular zone and subventricular zone consisting of PAX6+/SOX2+ NSCs) that form around central lumens. These 3D organoid cultures therefore provide a robust system amenable to extended cultivation and manipulation, which makes them a useful tool to model development and disease in the context of the complex brain microenvironment.

Recently, two protocols have been developed on enhancing cortical plate formation within hPSC-derived cerebral organoids: one using large spinner flasks and microfilaments as a solid support and another that uses a miniature spinning bioreactor termed Spin Omega (SpinΩ), which consists of 3D printed gears and paddles driven by a single electric motor. The SpinΩ provides an accessible and versatile format for culturing brain-region-specific organoids due to its reduced incubator footprint, decreased media consumption, and increased throughput, but several technical caveats limit its use in long-term experiments, most prominently the choice of components used to fabricate the device and the design of the device with respect to limiting the chances of contamination and mechanical failure.

SUMMARY

In one aspect, exemplary bioreactor systems can include a first frame and a second frame, a well plate, a motor plate, a motor, and a controller. The first frame may define a well plate inset and standoff insets for a first set of metal standoffs. The second frame may define a plurality of mounts and a plurality of insets for a second set of metal standoffs. In addition, a polymer collar may be coupled to each of the plurality of mounts. A gear may be positioned in each of the plurality of mounts. A paddle may be coupled to each of the gears. The well plate can be positioned within the well plate inset. The motor plate can be supported by and connected to the first set of metal standoffs and the second set of metal standoffs. The motor can be mounted on the motor plate and operatively connected to one of the plurality of gears. The controller can be in communication with the motor and configured to control a speed of the motor.

In another aspect, a method of using a bioreactor system is disclosed. The bioreactor system includes a first frame, a second frame, a well plate including a plurality of wells, a motor plate, a motor, and a controller, where the well plate is positioned within the first frame, where the second frame includes a plurality of mounts and a plurality of gears positioned in each of the plurality of mounts, where a paddle is coupled to each of the plurality of gears, and where the controller is in communication with the motor and configured to control a speed of the motor. The method can include adding media to each of the plurality of wells, initiating motor activation at a predetermined speed, adjusting a temperature of an environment surrounding the bioreactor system to a predetermined temperature range, adjusting a humidity of the environment to a predetermined humidity range, continuing motor activation for at least 60 days, ceasing motor activation after at least 60 days, removing the well plate from the first frame.

There is no specific requirement that a material, technique or method relating to bioreactor systems include all of the details characterized herein, in order to obtain some benefit according to the present disclosure. Thus, the specific examples characterized herein are meant to be exemplary applications of the techniques described, and alternatives are possible.

BRIEF DESCRIPTION OF THE DRAWINGS

FIG. 18A shows a schematic of the major stages in the culture protocol with key time points.

FIG. 19A shows four day-old embryoid bodies (EB) generated using microwells from Aggrewell. FIG. 19B shows relative growth of the embryoid bodies over time. (FIG. 19A: 0.5 mm, FIG. 19B—(C') 100 µm, (C") 50 µm, (C'") 100 µm.

FIG. 20A shows day 60 organoids showing the presence of neural progenitor markers Pax6 and Nestin. FIG. 20B shows cortical plate marker TBR1 shows the organization of the pre-plate. FIG. 20C shows MAP2 positive cells indicate the presence of committed neurons at this stage. Immunostainings were repeated on four brain organoids from three independent experiments. Scale bars: (A-C) 100 µm.

FIG. 21A shows Cajal-Retzius neurons stained for reelin show the presence of marginal zone. FIG. 21B shows staining for deep layer neurons (CTIP2) and neuronal markers (TUJ1). FIG. 21C shows upper-layer marker SATB2 indicates the presence of neurons belonging to the cortical layer IV. Immunostainings were repeated on four brain organoids from three independent experiments. Stitched images at 20×, scale bars: 500 µm.

FIG. 23A shows cells expressing Nestin and cleaved caspase 3 (Cl Caspase-3) at day 60. FIG. 23B shows at day 150 no structural compromise of the cortical architecture. CTIP2 (layer 5) and CUX1 (layer 2) markers of cortical layers are included for this time point. Immunostainings were repeated on four brain organoids from three independent experiments for day 60 and four brain organoids from one independent experiment for day 150.Scale bars: 100 µm. FIG. 23B is a stitched image.

DETAILED DESCRIPTION

Figure 1:
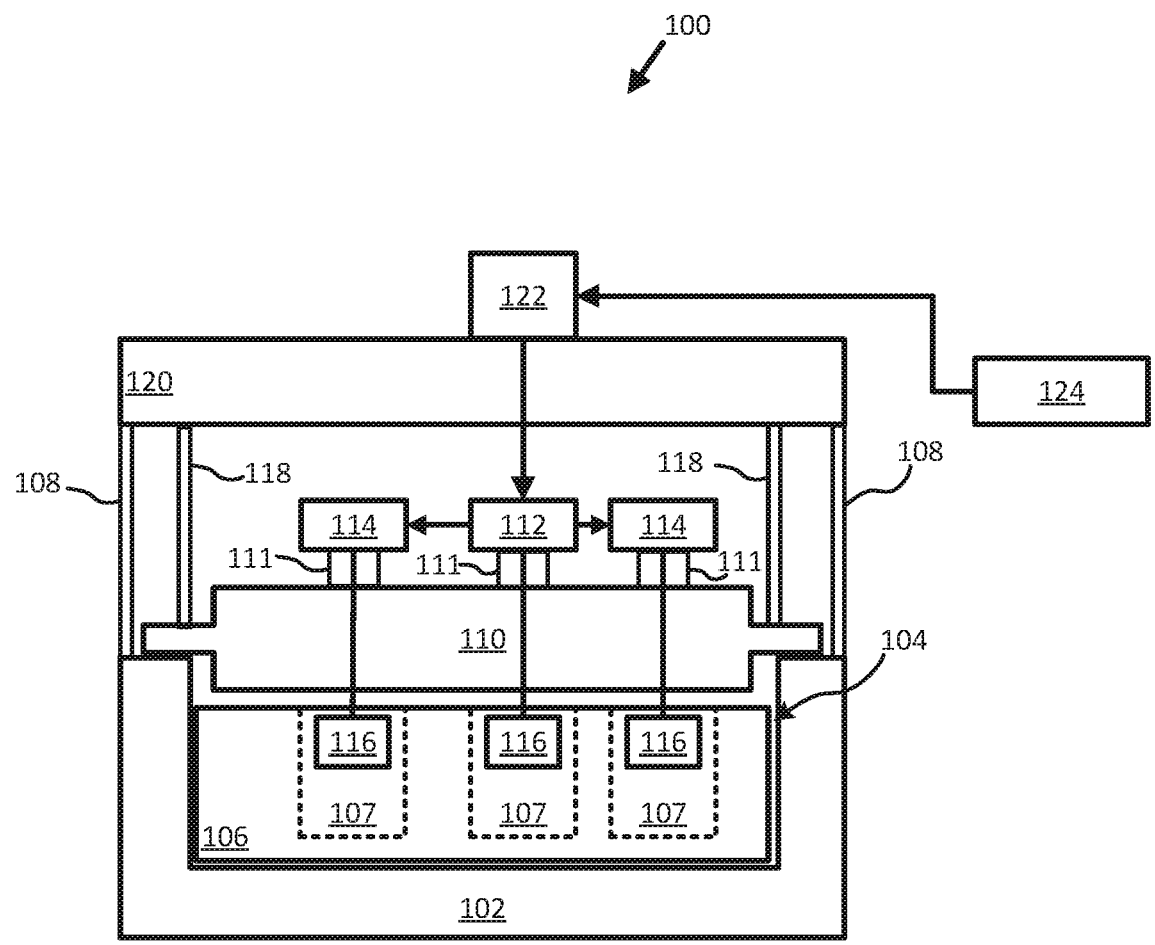
FIG. 1 shows a schematic, side sectional view of an example bioreactor system.
Figure 2A:
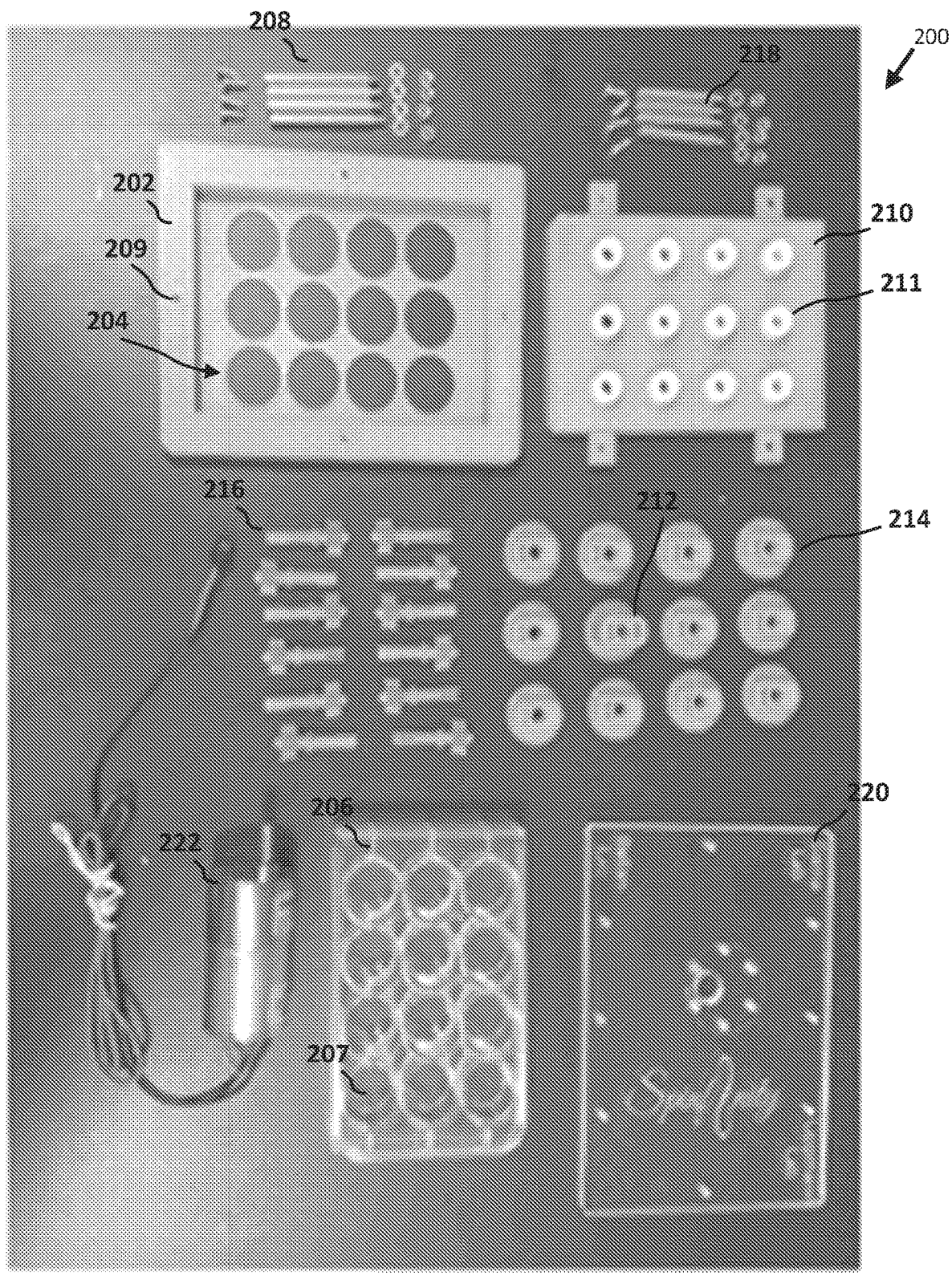
FIG. 2A shows components of an example bioreactor system.
Figure 2B:
FIG. 2B shows control-related components of the example bioreactor system.

Systems and methods disclosed and contemplated herein relate to bioreactor systems. Disclosed systems are particularly suited for brain organoids, which can be derived from human pluripotent stem cells.

Motor life span inside an incubator can be a major hurdle when using a bioreactor system because motors that are not designed to withstand harsh environments (high humidity and elevated heat) can easily corrode and break, leading to unexpected failures in the middle of long-term experiments. Exemplary systems disclosed herein may include a motor with the ability to operate at increased temperatures (typically with a maximum of 70° C.) and humidity (up to 90% humidity). Additionally, parylene vapor deposition may be applied to the motor to provide an additional moisture barrier to further the lifetime of the motor and increase durability.

Because of the humidity issue raised above, materials for certain components of exemplary bioreactor systems can be selected to reduce or resist chemical changes. Some implementations may use stainless steel screws, standoffs, nuts, and washers in order to reduce the oxidation of the metal and prolong the life of the bioreactor. Stainless steel parts also are autoclavable as separate components or with the assembled bioreactor, and exemplary designs can allow the majority of the equipment (including the 3D printed parts) to be assembled and autoclaved to reduce external handling and improve sterility.

Exemplary bioreactor systems also include an upper lid (where the motor is anchored), which may further enhance stability and consistency of the device. The SpinΩ motor was anchored in two points on the upper lid, which frequently caused the motor to waggle, thereby putting unnecessary and additional stress on the motor leading to eventual failure. Exemplary bioreactor systems may include a separate acrylic sheet, hex standoffs, and a larger, more durable motor, all components can be kept in perpendicular alignment to the well plate, thus preventing waggling. Additionally, because exemplary bioreactor systems may be designed with hex standoffs and an autoclavable 3D-printed first frame, the lid may be securely placed on the 12-well plate, which prevents spills and possible contamination points. By comparison, the original SpinΩ design freely rests on the top of the plate, making this design prone to spillage and contamination.

By addressing one or more of the aforementioned considerations, exemplary bioreactor systems may be miniaturized spinning bioreactors that are easy to maintain and perform consistently. Accordingly, exemplary bioreactor systems can be amenable to month-long experiments without concern of unexpected malfunctions.

Definitions

Unless otherwise defined, all technical and scientific terms used herein have the same meaning as commonly understood by one of ordinary skill in the art. In case of conflict, the present document, including definitions, will control. Example methods and materials are described below, although methods and materials similar or equivalent to those described herein can be used in practice or testing of the present disclosure. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

I. Exemplary Bioreactor Systems and Methods

FIG. 1 shows a schematic, side sectional view of example bioreactor system 100. As shown, bioreactor system 100 includes first frame 102, well plate 106, second frame 110, and motor plate 120. Bioreactor system 100 also includes wells 107, standoffs 108, mounts 111, gear 112, gears 114, paddles 116, standoffs 118, motor 122 and controller 124. In some instances, bioreactor system 100 may be positioned during operation inside an incubation device, where the incubation device may be configured to control the temperature and/or humidity of the environment therein. Various components are omitted from FIG. 1 for clarity, such as nuts and washers, and other embodiments may include more or fewer components. Relative sizes of components in FIG. 1 are not necessarily to scale.

First frame 102 defines well plate inset 104 sized to receive well plate 106. Well plate 106 defines a plurality of wells 107, which are typically cylindrical cavities. Wells 107 are typically similarly sized and evenly spaced about well plate 106. In various implementations, well plate 106 may define different quantities of wells 107. For example, well plate 106 may define 2 wells 107, 4 wells 107, 6 wells 107, 8 wells 107, 10 wells 107, 12 wells 107, 14 wells 107, 16 wells 107, 18 wells 107, or 20 wells 107.

First frame 102 also defines a plurality of standoff insets (not shown) for standoffs 108. Various quantities of standoffs 108 may be used, such as two standoffs 108, three standoffs 108, four standoffs 108, or six standoffs 108, along with a corresponding number of standoff insets. Typically, standoffs 108 are metal. Example metals usable for standoffs 108 include stainless steels.

Second frame 110 defines a plurality of mounts 111 and standoff insets (not shown) for standoffs 118. Mounts 111 receive gears 112 and 114. Typically, a number of mounts 111, gears 112 and 114, and paddles 116 corresponds to the quantity of wells 107 in well plate 106. For instance, in implementations with twelve wells 107, bioreactor system 100 may include twelve mounts 111, twelve gears 112 and 114, and twelve paddles 116. In some instances, a polymer collar (not shown) may be coupled to each of the plurality of mounts 111.

Gear 112 is in mechanical communication with motor 122. Rotation of gear 112 causes rotation of adjacent gears 114 (shown with arrows in FIG. 1). A paddle 116 is coupled to each gear 112 and 114.

Rotation of gears 112 and 114 also causes rotation of paddles 116. Certain gears 114 rotate clockwise (CW) and certain gears 114 rotate counterclockwise (CCW), depending on the rotation of adjacent gears 114. Paddles 116 are positioned within wells 107 and typically include a single blade, two blades, three blades, or four blades. A relative height of paddles 116 in wells 107 can be determined so as to agitate contents of wells 107 as desired.

Motor plate 120 includes a plurality of insets to receive standoffs 108 and 118, and thereby motor plate 120 may be supported by standoffs 108 and 118. Motor plate 120 also supports motor 122. In some implementations, motor plate 120 is made of an acrylic material, although other materials are contemplated.

Motor 122 is operatively connected to gear 112 and may drive gear 112 at a desired speed. Controller 124 is in communication with motor 122 and can be programmed to control a speed of motor 122. Controller 124 may include a processing unit and memory storing instructions that, when executed by the processing unit, cause the controller 124 to communicate one or more rotational speeds to motor 122. In alternate implementations, controller 124 may be a system on a chip (SoC) programmed to control a speed of motor 122. In some implementations, controller 124 may include a bridge, such as an L298n bridge, in communication with a controller, such as a Raspberry Pi 3A+. In some instances, a touchscreen interface is in communication with the controller.

In various implementations, controller 124 may be programmed to cause the motor 122 to rotate at 10 rotations per minute (RPMs); 20 RPMs; 30 RPMs; 40 RPMs; 50 RPMs; 60 RPMs; 70 RPMs; 80 RPMs; 90 RPMs; or 100 RPMs. In some instances, controller 124 may be programmed to cause the motor 122 to rotate at 20-40 RPMs; 30-50 RPMs; 40-60 RPMs; or 35-45 RPMs. In some instances, controller 124 may be programmed to cause the motor 122 to rotate clockwise or counterclockwise.

In some instances, exemplary bioreactor systems 100 can include one or more of the following aspects. For instance, an exemplary bioreactor system may have increased motor life-span under high temperature and humidity conditions; may have the ability to be autoclaved after assembly, thereby eliminating a need for disassembly for cleaning and sterilization; can have an enclosed assembly to reduce spills and leaks; and/or may have an integrated touch screen display enabling a user to change motor speed.

A. Exemplary Embodiment of a Bioreactor System

Figure 3:
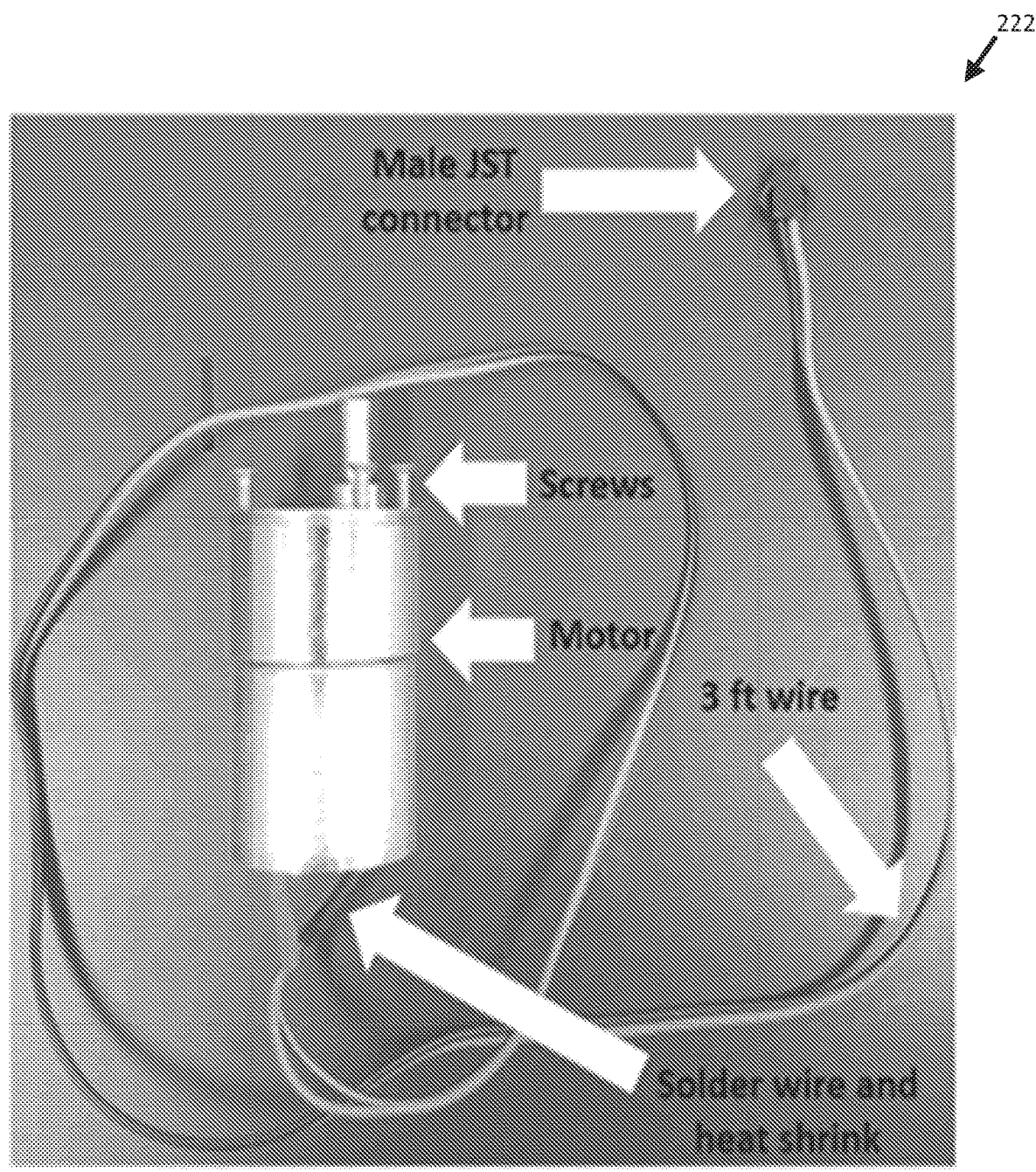
FIG. 3 shows an example motor assembly of the system shown in FIG. 2A.

An exemplary embodiment of a bioreactor system 200 was built and photographs of various components are shown in FIG. 3A and FIG. 3B. Bioreactor system 200 was built primarily from 3D printed polyetherimide (PEI) resin, ULTEM™ 1010 resin to permit autoclaving. Alternate 3D printing filaments, such as acrylonitrile butadiene styrene (ABS), can be used but may require more extensive sterilization steps such as sequential washes in 10% bleach, 70% ethanol, distilled water washes and UV radiation.

The bottom 3D printed frame 202 defined an inset 204 to hold a 12-well plate 206, as well as inserts 209 for the metal standoffs 208. The first frame 202 was sized to hold a 12-well cell culture plate 206 where organoids were cultured.

The top 3D printed frame 210 housed polytetrafluoroethylene (PTFE) collars 211, gears 212 and 214, and paddles 216, which were manually assembled. The 12-Well Plate Lid 210 (also referred to as the second frame) held the PTFE collars 211, CCW Paddles 216, CW Paddles 216, Gears 214, and Motor Shaft Gear 212. The second frame 210 component replaced a traditional lid on a cell culture plate. Each CCW Paddle 216 was partially submerged in the media and carried out mixing in a counterclockwise direction. Each CW Paddle 216 was partially submerged in the media and carried out mixing in a clockwise direction. Each gear 212 and 214 held the paddles 216 and spun under the control of the motor 222.

Motor shaft gear 212 connected to the motor 222 and turned the other gears 214. Gear 212 connected directly to a DC 12V 100RPM gear motor 222 (Greartisan) attached to an acrylic motor plate 220. The acrylic motor plate 220 rested on the metal standoffs 208 and 218 and was screwed into place for sturdiness. All components could be optionally coated with parylene to prevent corrosion of the metal housing on the motor and to add an additional hydrophobic barrier to prevent absorption of media into the 3D printed parts. The motor 222 connected to a L298n bridge and a Raspberry Pi 3A+ (see 224 in FIG. 3B) that controlled the motor speed through a touchscreen interface without a keyboard or mouse.

A Parylene Template for Gears held the gears during parylene deposition. This print is optional if the user will not coat with parylene. A Parylene Template for Paddles held the paddles during parylene deposition. This print is optional if the user will not coat with parylene. A X4 L298n Bridge Holder held four individual bridges for driving the motors. 5 Motors is a python script that was used to enable touchscreen control over motor speed and direction.

B. Embodiment of a Method for Using an Exemplary Bioreactor System

Exemplary bioreactor systems disclosed and contemplated herein can be used in a variety of ways. An example method includes first adding media to each of the plurality of wells in an example bioreactor system. Exemplary media is typically formulated for generating brain organoids. In some instances, the bioreactor system including the media may be positioned within an incubation device.

Next, motor activation is initiated at a predetermined rotational speed. As discussed above, the rotational speed may vary depending upon test conditions and media. Example rotational speeds may be between 10 RPM and 100 RPM A controller may receive one or more instructions from a user via an input device, such as a touchscreen computing device.

In some implementations, a temperature of an environment surrounding the bioreactor system may be adjusted to a predetermined temperature range. In some implementations, the predetermined temperature range may be between 40° C. and 70° C.

In some implementations, a humidity of an environment surrounding the bioreactor system may be adjusted to a predetermined humidity range. In some implementations, the predetermined humidity range may be between 40% and 90%.

Depending upon the target end product, motor activation may be continued for varying time periods. In some implementations, motor activation may be continued for at least 60 days; at least 120 days; at least 150 days; or at least 200 days. Typically, the motor speed is constant during the time period of operation.

After motor activation for a given amount of time, motor activation is ceased. Ceasing motor activation may occur after at least 60 days; after at least 120 days; after at least 150 days; or after at least 200 days. After motor activation ceases, the well plate may be removed from the first frame.

C. Embodiment of a Method for Assembling an Example Bioreactor System

Various methods can be used to assemble example bioreactor systems disclosed and contemplated herein. In example embodiments, hardware assembly, electronics assembly, and media changes can include one or more of the following operations.

1. Example Hardware Assembly

An example method of assembling various hardware components of an example bioreactor system can include one or more of the following operations. A first operation includes soldering positive and negative terminals (3 ft of 2 wire cable). Then tubing can be heat shrunk to each terminal. Then male versions of JST plugs are crimped on and 6 screws are loosely added to the motor (see FIG. 3). In some instances, the motor can be coated with parylene.

Figure 4:
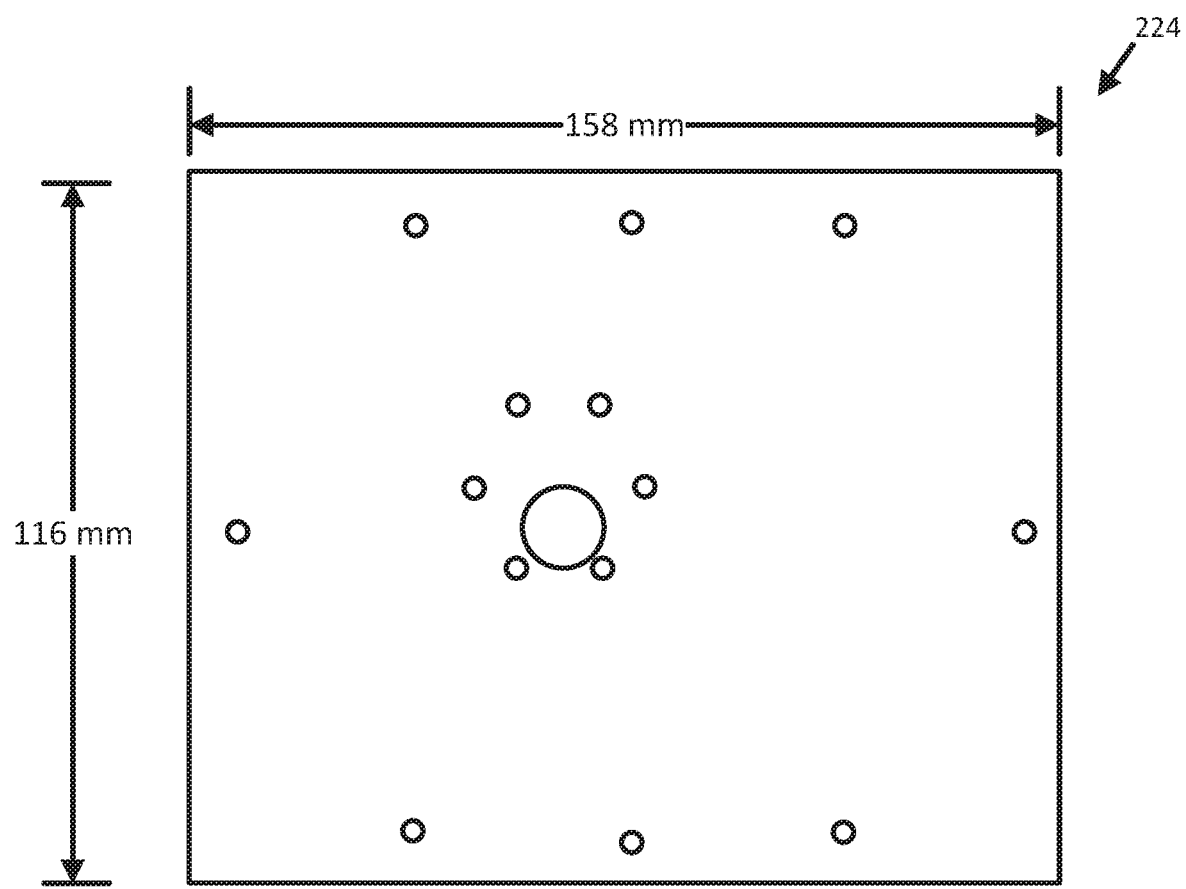
FIG. 4 shows an example motor plate dimensions for cutting.

An acrylic motor plate can be prepared by laser cutting the acrylic plate with appropriate dimensions. An example acrylic motor plate is shown in FIG. 4. Settings can vary based on laser wattage. In one implementation, a 45 W laser cutter was used with 80% power and 70% speed with two passes.

Bioreactor assembly can include one or more of the following operations. In some instances, a 3D-printed 12 well plate lid and first frame are coated with parylene. In some instances, paddles and gears are attached to the 3D printed holders and then coated with parylene. Placing the bottom of the gears facing up can maximize vapor deposition. The stainless steel M3 nuts can be inserted into the gears. Then a 5 mm (diameter of teflon collar) drill bit can be used to gently core out the center of the teflon collar and insert into the 12-Well Plate Lid. This can include lightly drilling out the center of the teflon collar and removing as little as possible.

Figure 5B:
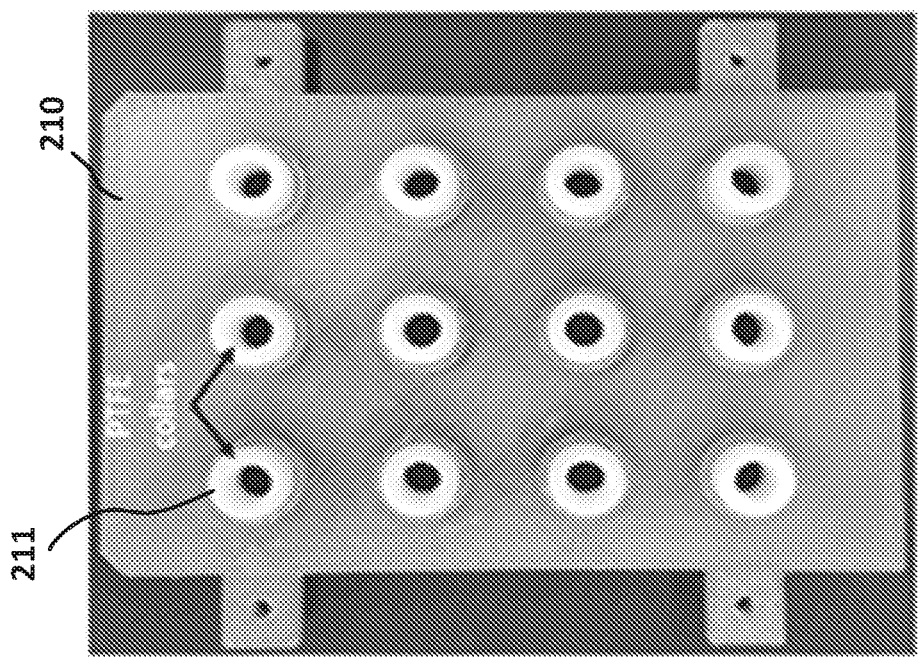
FIG. 5B shows positioning of PTFE collars on an opposite side of the second frame.
Figure 5A:
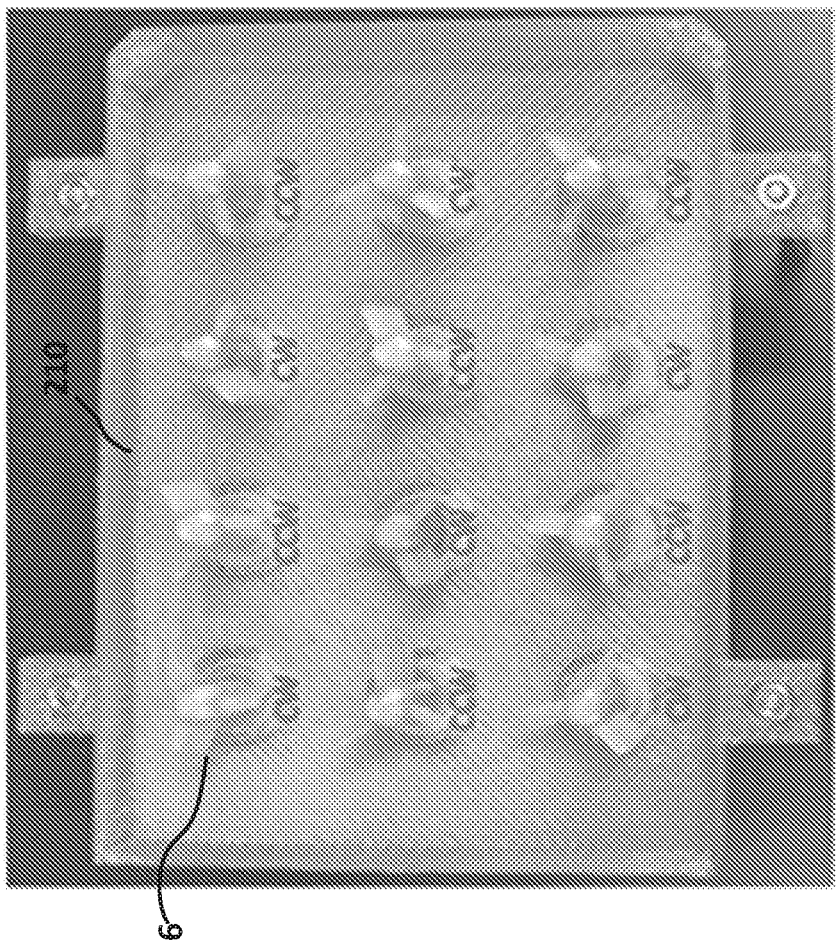
FIG. 5A shows insertion of paddles into a 12-well plate lid (the second frame) of the system shown in FIG. 2A, where positioning of the clockwise (CW) and counterclockwise (CCW) paddles are noted.

Next, clockwise (CW) paddles and counterclockwise (CCW) paddles are inserted into the second frame and PTFE collars (see FIG. 5A and FIG. 5B). FIG. 5A shows possible positioning for each paddle on one side of the second frame 210 and FIG. 5B shows mounts 211 with PTFE collars on the opposite side of the second frame 210.

Figure 6:
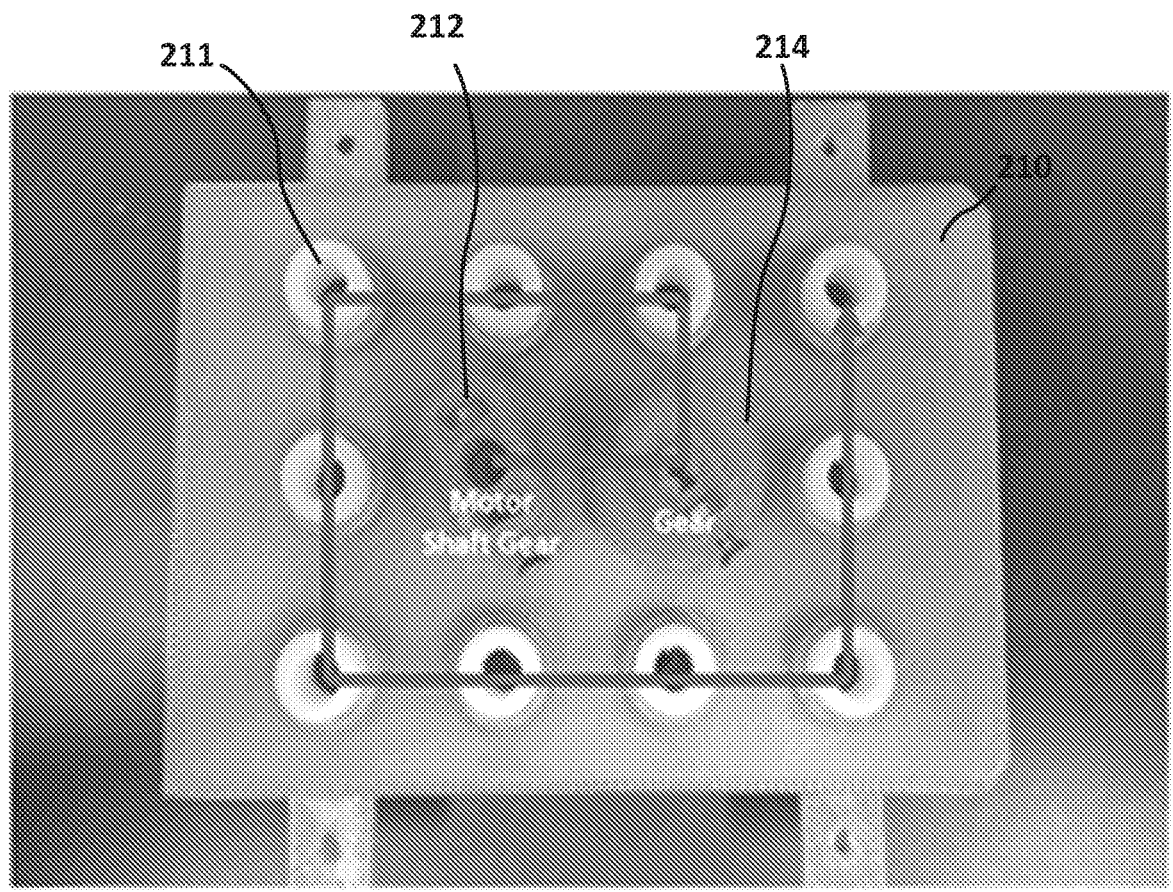
FIG. 6 shows an assembly pattern of the gears of the bioreactor system shown in FIGS. 2A and 2B. A position of the motor shaft gear is also shown.
Figure 7A:
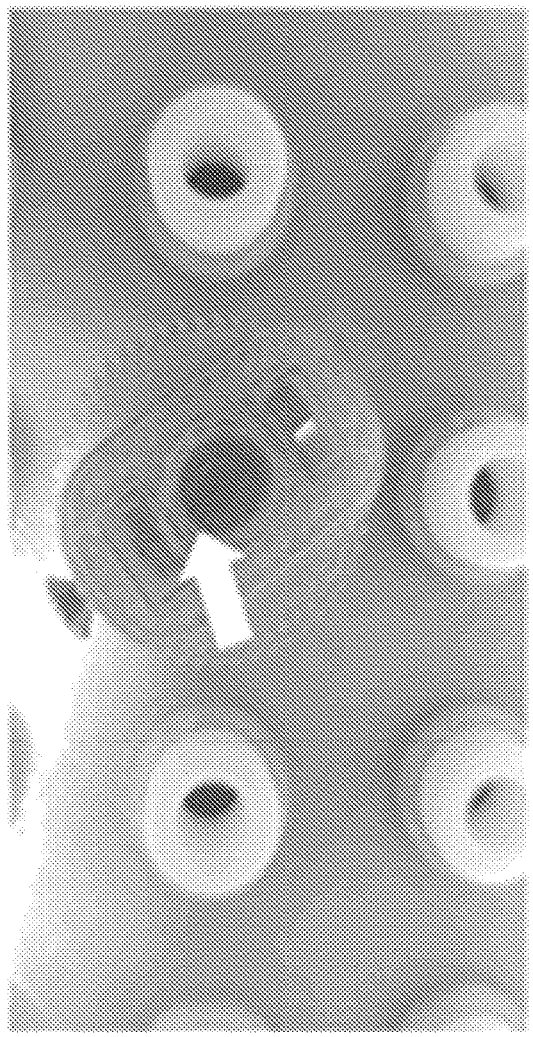
FIG. 7A shows positioning of screws in an example gear before tightening and FIG. 7B shows after tightening.
Figure 7B:
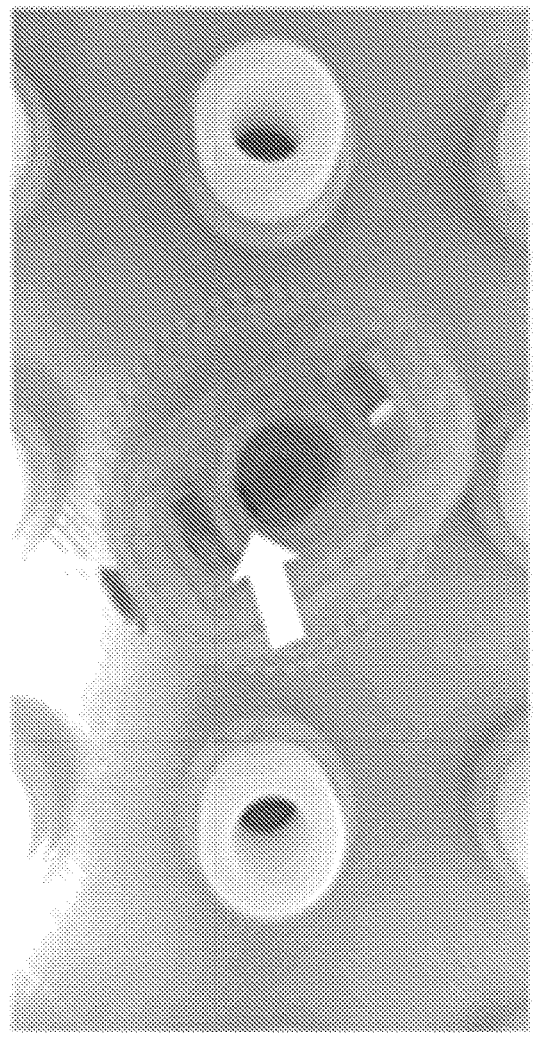

To attach the gears, the operation starts with the motor shaft gear 212 at the B2 position, which is the second row, second column of the mounting array (FIG. 6). The bottom set screw gear needs to be aligned with the opening on the paddle. Screw in the top screw. The shaft should easily and freely spin (FIG. 7A and FIG. 7B).

Next, the other gears 214 are attached to the rest of the mounts 211 working counterclockwise around the lid (FIG. 6). The teeth of the gears should be aligned and interlock.

Figure 8A:
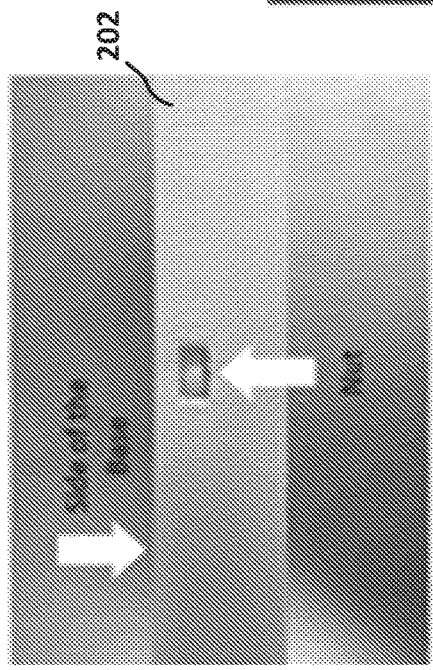
FIG. 8A shows attachment of 45 mm hex standoffs to first frame of the bioreactor system in FIG. 2A, where a nut is placed into the side of the first frame.
Figure 8B:
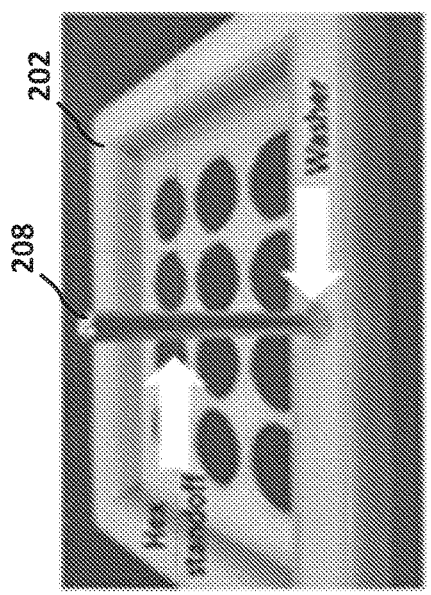
FIG. 8B shows a washer added to the 45 mm hex standoff, which is then screwed into the nut.
Figure 8C:
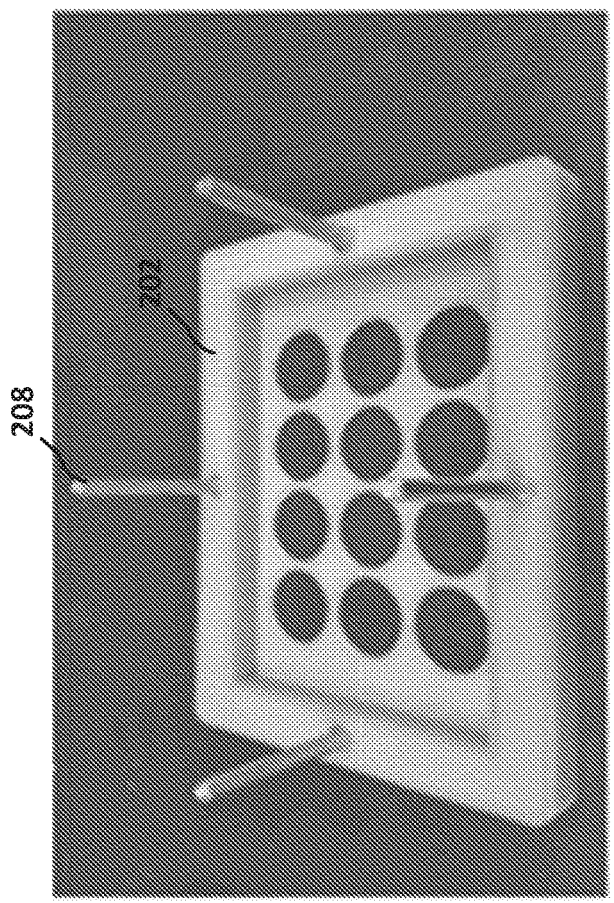
FIG. 8C shows all hex standoffs attached to the first frame.

Next, the hex standoffs 208 and 4 hex nuts are attached to the first frame 202 (FIG. 8A, FIG. 8B, and FIG. 8C). The 45 mm hex standoffs 208 are screwed on with washers attached to the 4 locations with the hex nuts on the first frame 202, and screws are attached to hex standoffs 208.

Figure 9:
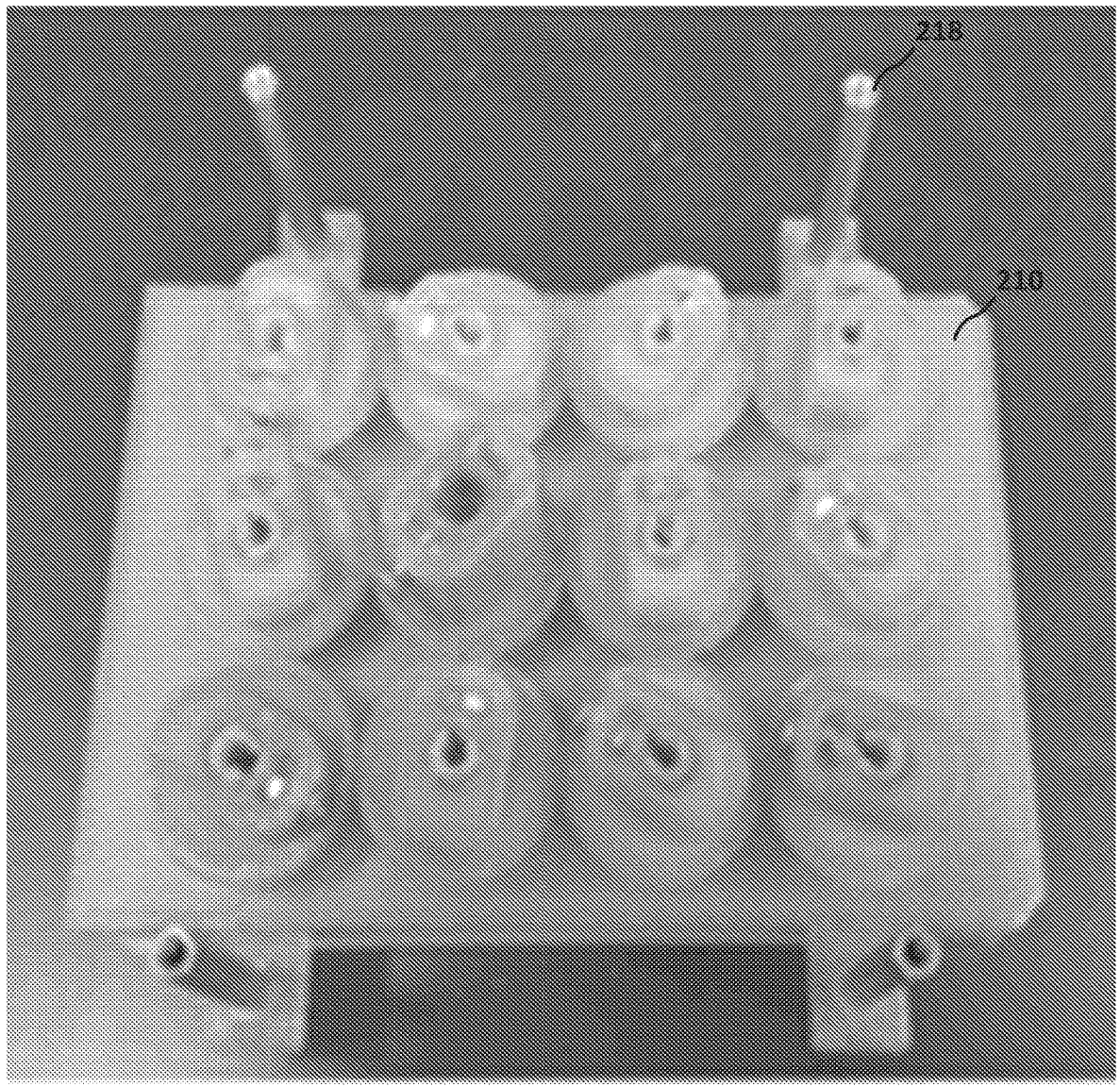
FIG. 9 shows attachment of 35 mm hex standoffs to the 12-well plate lid (the second frame).
Figure 10:
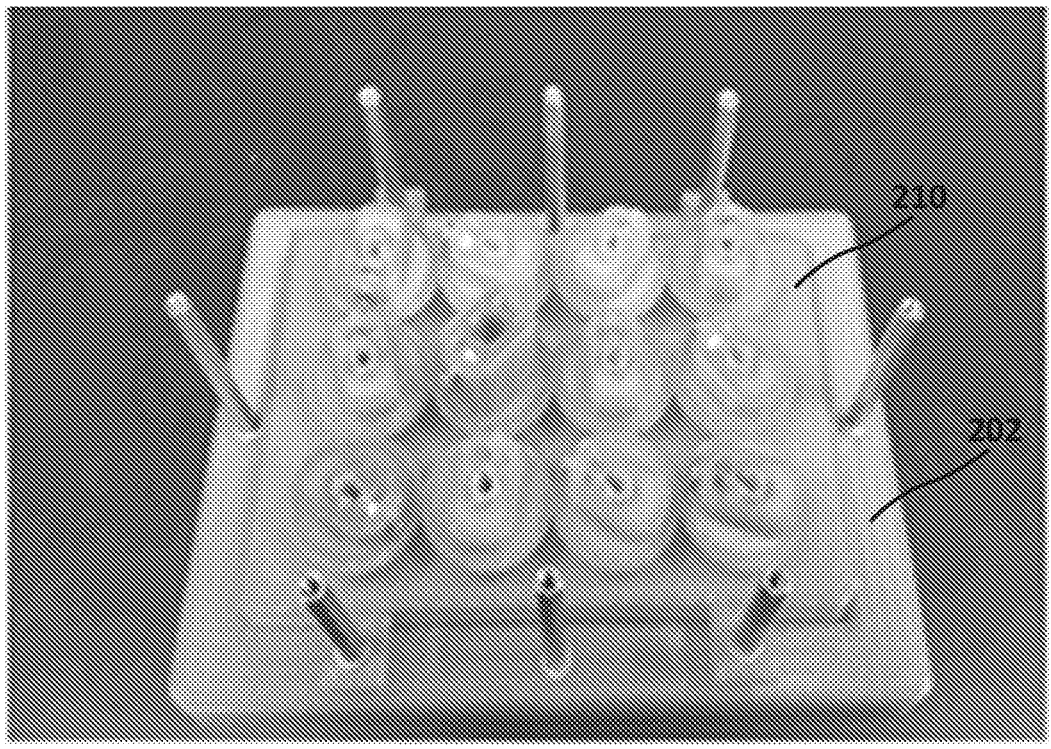
FIG. 10 shows the assembly of FIG. 9 positioned within the assembly of FIG. 8C.

Then the hex standoffs 218 are attached to the second frame 210 and the nuts are inserted into the 12-Well Plate Lid (the second frame 210) (FIG. 9). The 35 mm hex standoffs are screwed in with washers attached to all the locations with the hex nuts on the second frame 210 and screws are attached to the hex standoffs. The second frame 210 may then be positioned in the first frame 202 (FIG. 10).

Figure 11:
FIG. 11 shows the first frame with the hex standoffs, the second frame with the paddles and gears placed upside down in an autoclavable bag.

Next, the 3D printed and stainless-steel parts either assembled or as individual pieces are autoclaved for 60 minutes (FIG. 11). All autoclavable items may be placed in an autoclavable bag upside down, and the bag sealed. Everything but the motor, acrylic plate, and cell culture plate can be autoclaved.

Figure 12:
FIG. 12 shows attachment of the motor to the acrylic motor plate.
Figure 13:
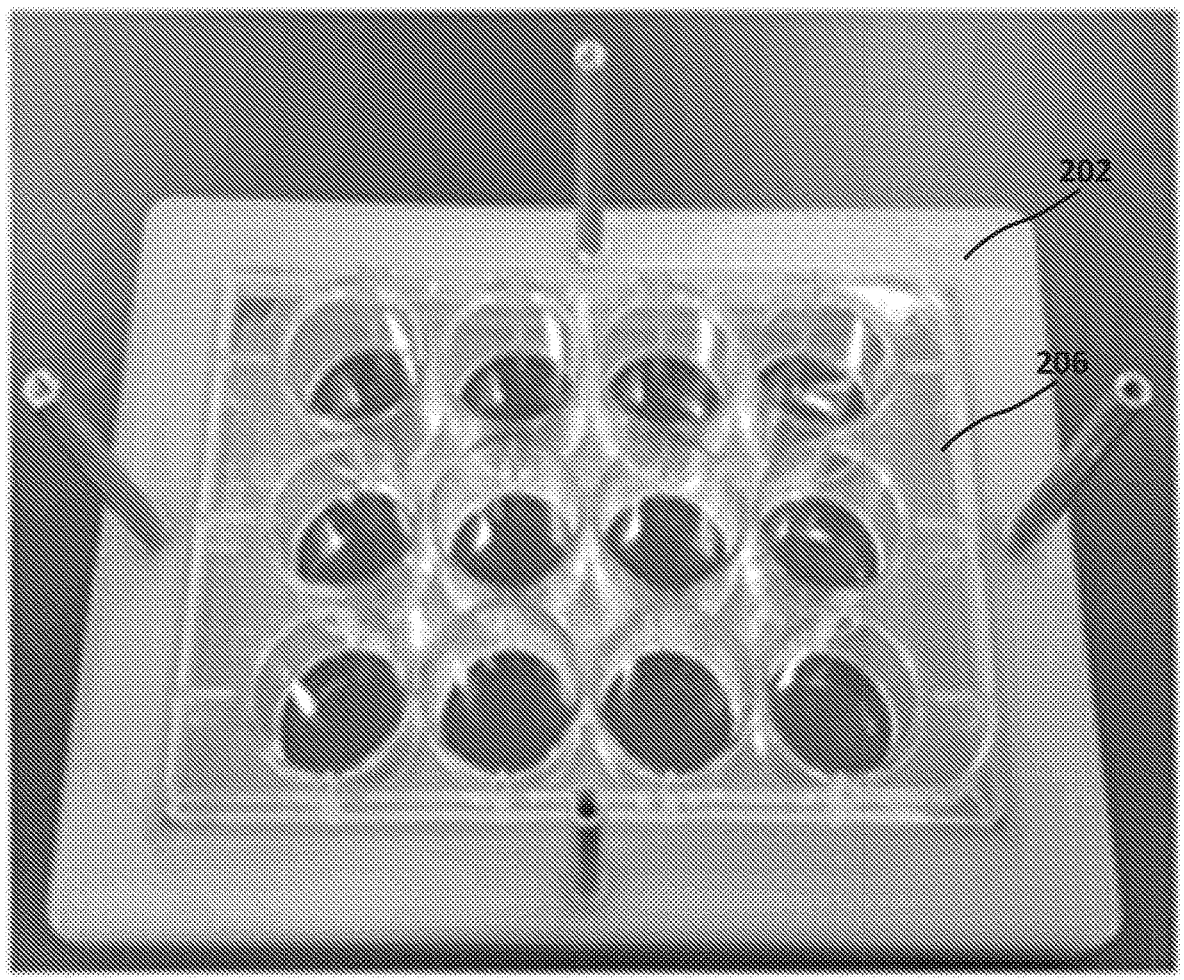
FIG. 13 shows placement of a 12-well plate into the first frame.

After autoclaving is complete, the autoclave bag is sprayed with 70% ethanol and transferred into a biosafety hood. After taking the assembly out of the bag, the shaft of the motor may be inserted through the hole in the acrylic plate 220, and the motor attached to the acrylic plate 220 using the six 10 mm screws (FIG. 12). The motor and acrylic plate can be transferred into the biosafety hood and the motor and acrylic plate should be sprayed with 70% ethanol for sterilization. The second frame is removed from a sterile 12-well plate and placed into the first frame (FIG. 13) and then the second frame may be placed on the top of the first frame.

Figure 14:
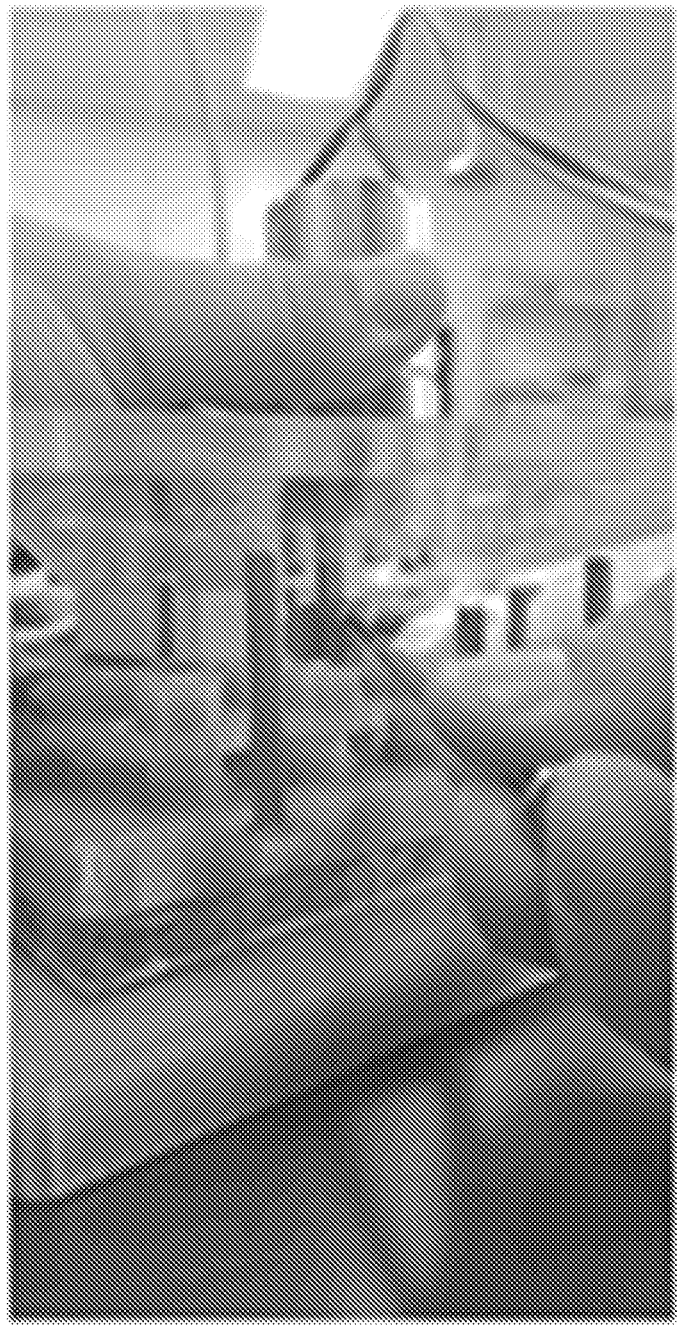
FIG. 14 shows attachment of the beveled side of the motor shaft into the motor shaft gear.

Next, the screws are removed from the hex standoffs, and the screws can be stored in a sterile petri dish. Then the top screw on the Motor Gear Shaft is loosened. Next, the acrylic sheet is placed on top of the hex standoffs. The motor shaft goes inside the Motor Shaft Gear (FIG. 14).

Then attach the motor to the Motor Gear Shaft. Find the beveled side of the motor shaft and line it up with the top screw of the Motor Shaft Gear. By hand, screw the top screw to where there is a little play with the set screw in the shaft. Care should be taken to not overtighten the top screw of the Motor Gear Shaft.

Figure 15:
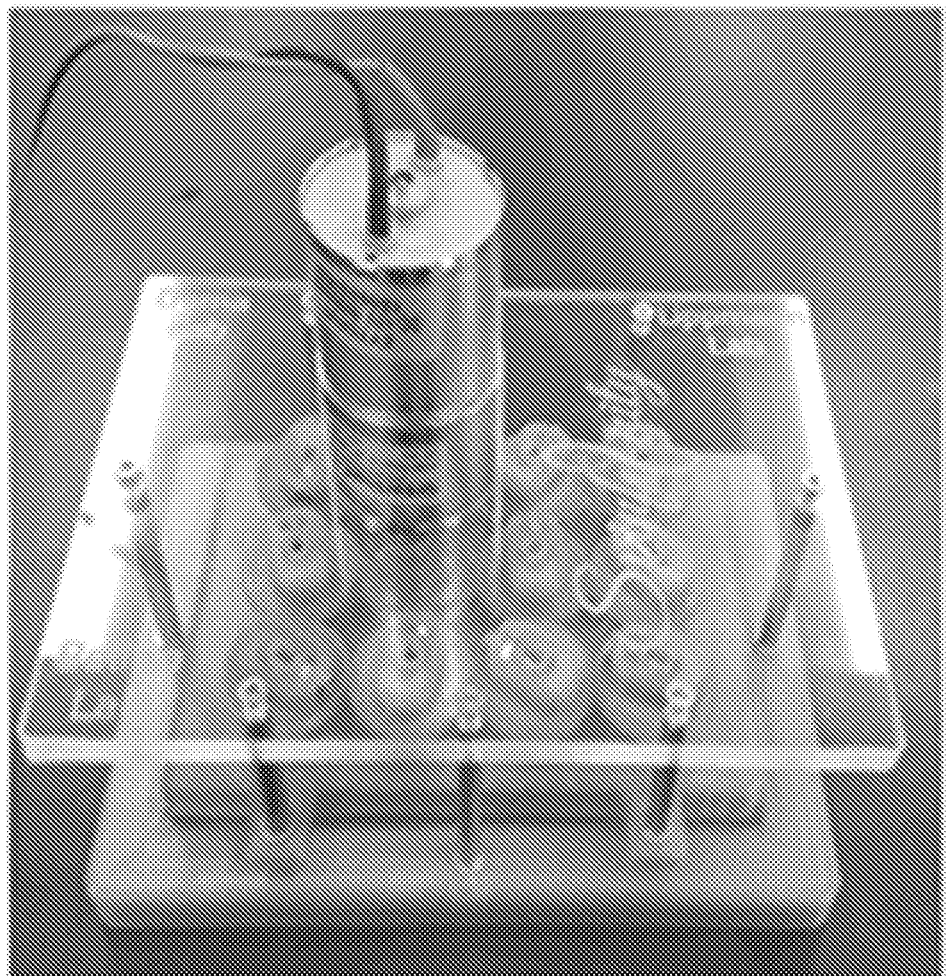
FIG. 15 shows an assembled bioreactor system.

Next, thread the screws into the 35 mm hex standoffs (on the second frame) through the acrylic plate (FIG. 15) being careful to not tighten completely. There should be some play. Then thread the screws through the acrylic plate to the 45 mm hex standoffs on the first frame, and tighten all four screws. These should be securely tightened.

Next, tighten the screws attached to the 35 mm hex standoffs. Once fully tightened, turn the screws ½ counter clockwise. The screws to the second frame hex standoffs are designed to be loose. Before using with cells, the assembled bioreactor may be run for at least 24-48 hours dry in a 37° C. incubator to remove any debris from the 3D printed parts. Sterile PBS can then be used to wash the bioreactor.

2. Example Electronics Assembly

An example method for assembling electronic components of an example bioreactor system can include one or more of the following operations. First, follow the Raspberry Pi Touchscreen assembly instructions with the Raspberry Pi 3 A+ and Raspberry Pi SD card preloaded with Noobs. The Raspberry Pi should be powered by the 5V micro-USB power source provided in the kit.

Figure 16:
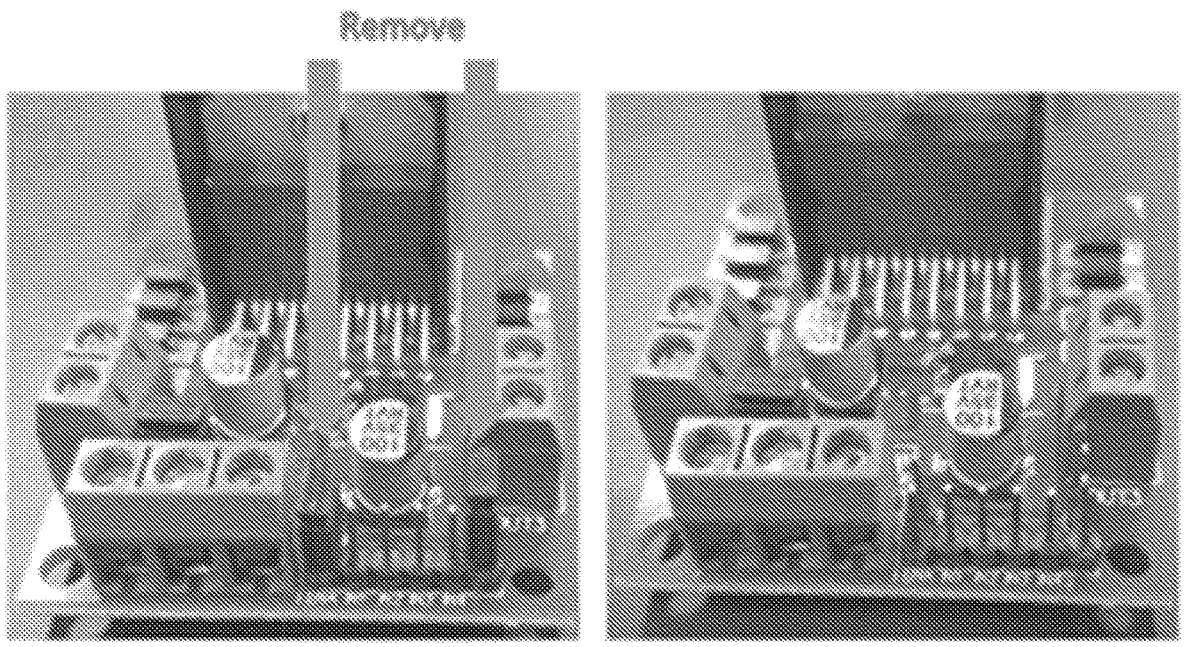
FIG. 16 shows removal of jumpers from a L298n bridge.
Figure 17:
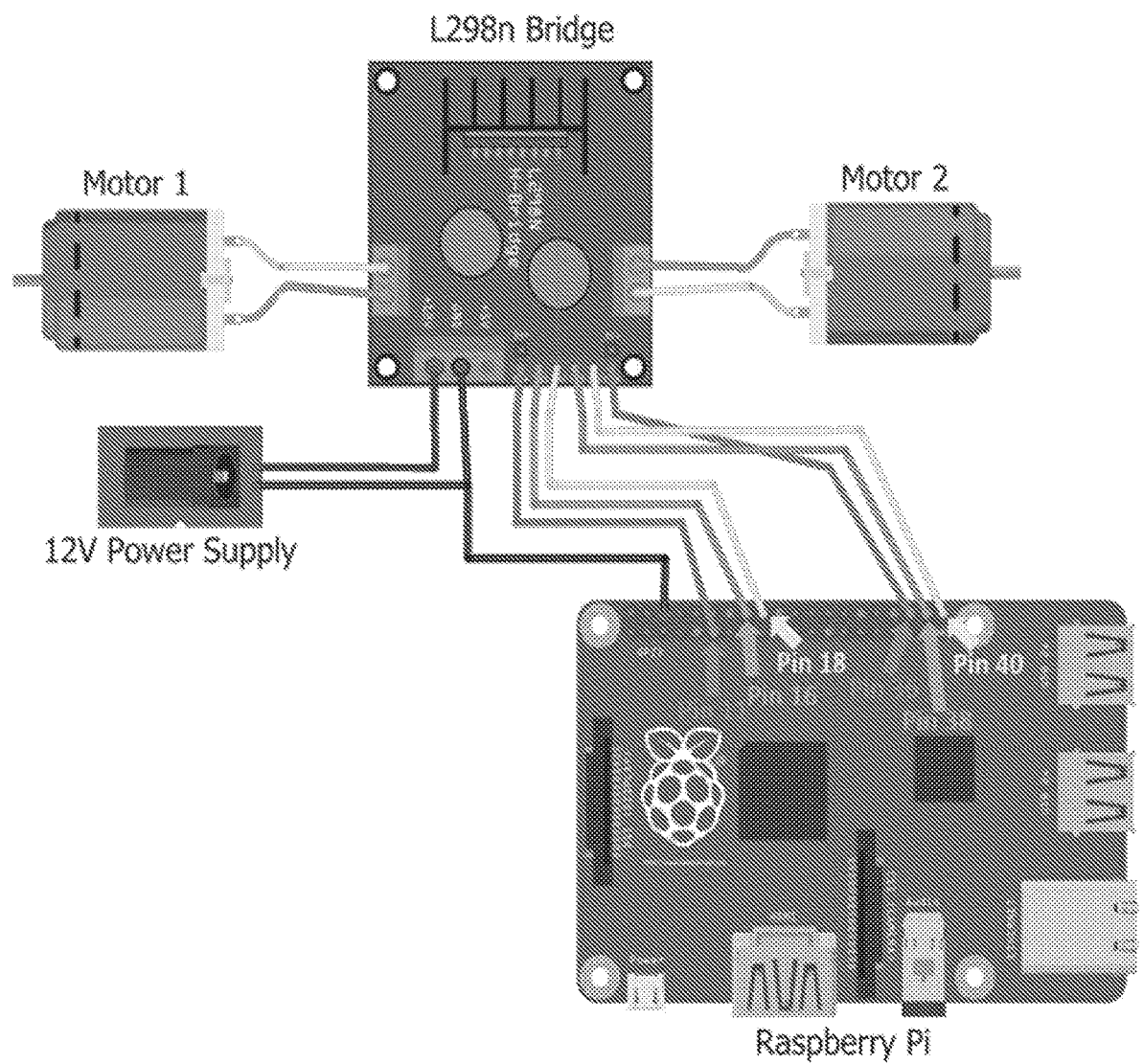
FIG. 17 shows an example for how to connect an L298n bridge to two motors and a Raspberry Pi.

Once the touchscreen has been assembled, the electronics should be assembled as described below. First, the jumper is removed from enable A and B on the L298n bridge (FIG. 16). Then the bridge is connected to the GPIO pins on the Raspberry Pi (FIG. 17). For the first motor, connect the ENA pin on the L298n bridge to GPIO pin 11, connect IN1 on the L298n bridge to GPIO pin 16 and connect the IN2 on the L298n bridge to GPIO pin 18 (FIG. 17). Repeat this for all motors and L298n bridges. Each L298n bridge can control two motors, and using the instructions in FIG. 17, a single Raspberry Pi can run up to five motors.

Then connect the in-line power toggle to turn the bridge on and off. Make sure the L298n bridge has a 12V input. The ground wire goes to the bridge and the Raspberry Pi—the system may not work without both grounds. Last, connect 3 feet of 2-wire to the output screw terminals for motor 1 and attach a female JST connector on the other end.

3. Example Media Changes

Example media changes can include one or more of the following operations. First, turn off the motor using the in-line power switch and disconnect the JST connector. Take the bioreactor system out of the incubator and place in a biosafety hood. Then unscrew the screws attached to the 45 mm hex standoffs.

Next, transfer the second frame (that is still attached to the acrylic plate and motor) to a sterile, empty 12 well plate. This will expose the plate of organoids resting in the first frame, which can be removed for imaging if desired.

Then, change the media on the organoids. Tilt the plate approximately 45 degrees so that the organoids will sink to the bottom of the well. Carefully remove the media from each well using a P1000 micropipette and put the spent media into an empty 15 mL conical. Check the spent media to make sure that no organoids were accidentally removed. Once spent media is removed, add 3-4 ml of fresh media to each well using a P1000 micropipette.

Then return the second frame on top of the 12-well plate that is resting in the first frame. Screw the screws back onto the 45 mm hex standoffs tightly. Put the device back into the incubator. Connect the JST connector and turn on the motor. Check to make sure that the gears and paddles are turning at the desired speed.

II. Example Experimental Data

Exemplary systems were tested experimentally and the results of the data are discussed below.

Figure 19A:
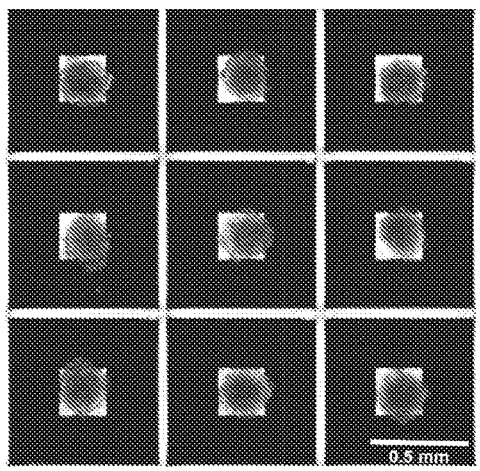
FIG. 19A and FIG. 19B show embryoid body generation and size over time.
Figure 19B:
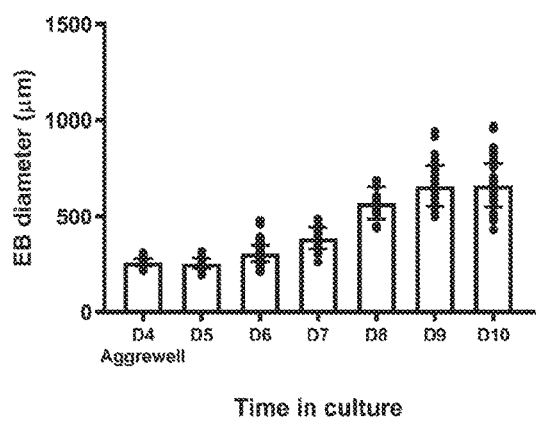

Brain organoids were generated using the STEMdiff™ Cerebral Organoid Kit (Stem Cell Technologies) with the embodiment of example bioreactor system shown in FIGS. 2A-17. As the generation of homogeneous embryoid bodies (EBs) is critical for achieving homogenous organoids, we utilized a 24-well plate AggreWell™ 800 (Stem Cell Technologies, catalog 34815) to increase the reproducibility and the yield of EBs (FIG. 19A and FIG. 19B).

Figures 18A, 18B:
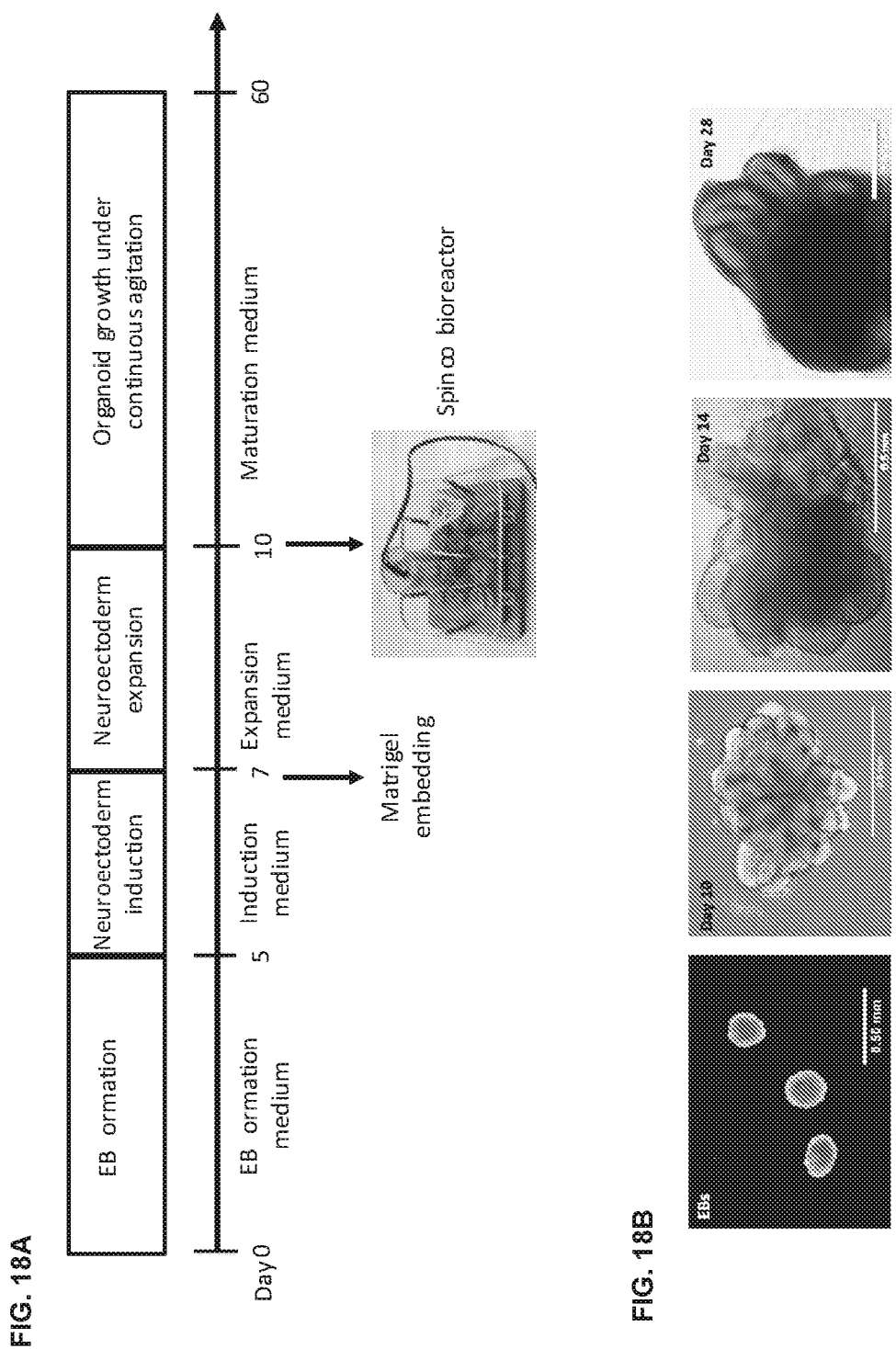
FIG. 18A shows a protocol for the generation of brain organoids using an embodiment of a bioreactor system.
FIG. 18B shows macroscopic images (taken with inverted microscope) of brain organoids at different developmental stages. Scale bars: 0.5 mm.
Figure 19C:
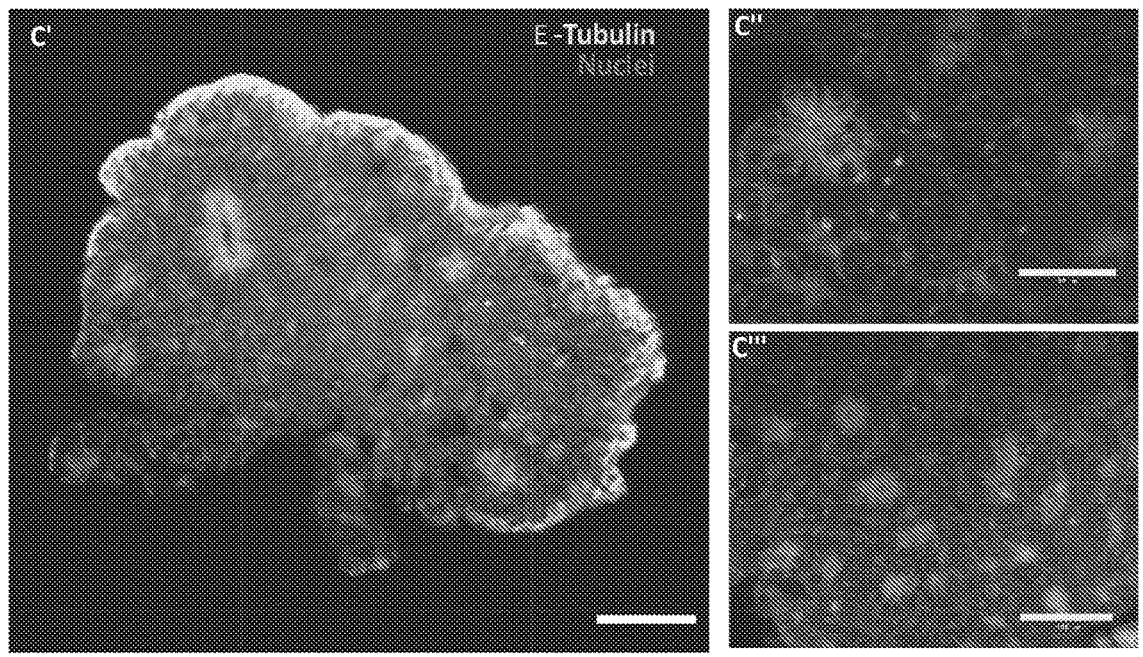
FIG. 19C shows light sheet microscope images of day 7 embryoid body showing the formation of organized neural rosettes; where C" and C'" show close up to the neural rosettes. Data are mean±s.d. Scale bars.

After 4 days of culture in the AggreWells, the organoids were transferred to a 10 cm ultra-low attachment plate to allow further growth of the EBs before the Matrigel embedding process (FIG. 18B). The diameter of the EBs increased over time; by the embedding day (day 7) the average diameter was 387 μm (±57) and by the bioreactor transfer day (day 10) the average diameter was 661 μm (±112) (FIG. 19B). High resolution images show the formation of organized neural rosettes within the EBs at day 7 (FIG. 19C). Alpha-tubulin (α-tubulin filaments) can be seen organized radially from the lumen (FIG. 19C). These polarized neuroepithelium-like structures resemble neural tube formation and are the precursors to the formation of the brain lobules.

Figure 20A:
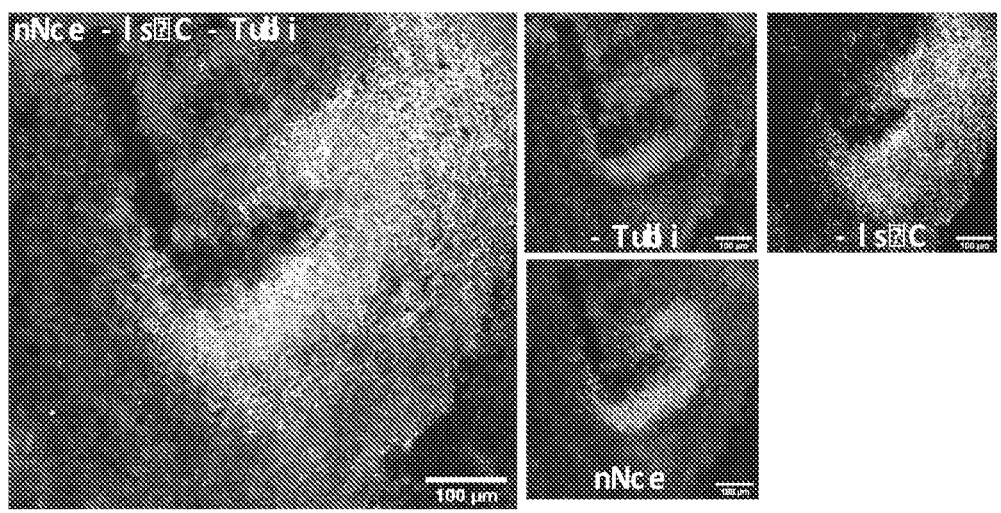
FIG. 20A-FIG. 20C show staining for neural progenitor cells and cortical neurons.
Figure 20B:
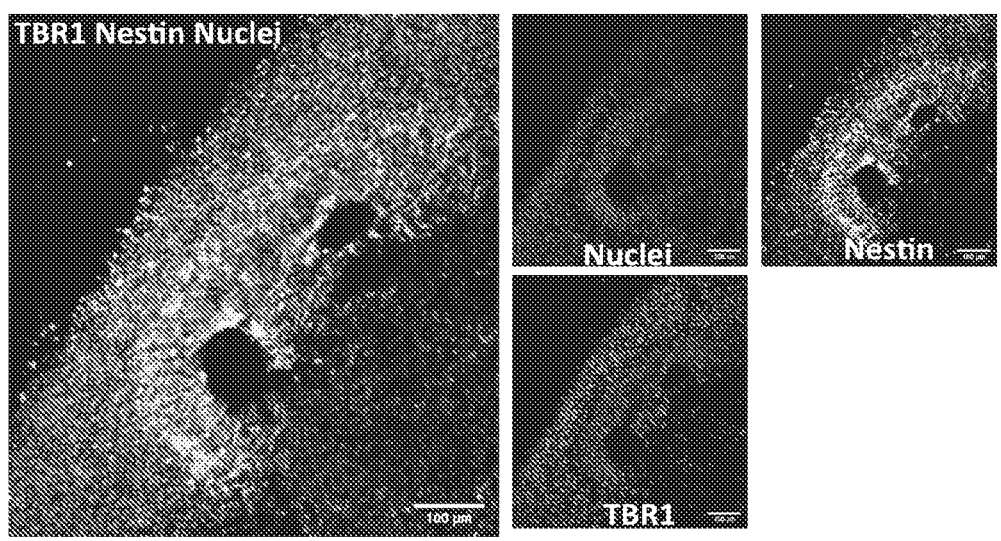
Figure 20C:
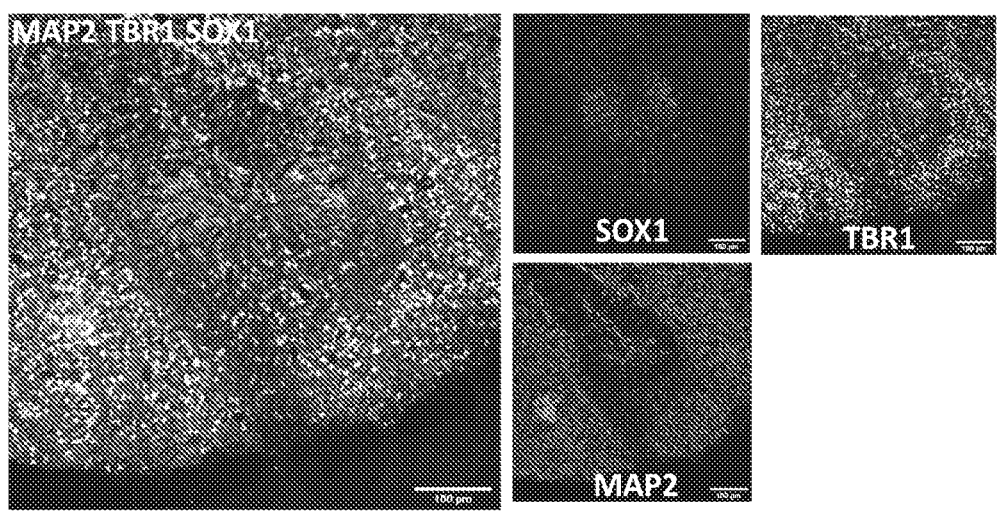

Characterization of the organoids were was performed at day 60 (4 technical replicates in each of the three biological replicates (n=3)) and day 150 (4 technical replicates in one biological replicate (n=1)). Organoids were fixed in 4% paraformaldehyde (PFA) for 15 min at 4° C., followed three 5 min washes in phosphate-buffered saline (PBS) and 30% sucrose dehydration overnight at 4° C. Embedding for sectioning was performed as reported previously in M. A. Lancaster, M. Renner, C. A. Martin, D. Wenzel, L. S. Bicknell, M. E. Hurles, T. Homfray, J. M. Penninger, A. P. Jackson, J. A. Knoblich, "Cerebral organoids model human brain development and microcephaly," Nature, 501 (2013), pp. 373-379. Cryosections (15 µum thick) were stained using neural progenitor cell (NPC), mature pan-neuronal, and cortical layer markers. As previously reported for day 60 organoids, the cells that stain positive for neural progenitor markers are localized in the periphery to the ventricle-like structures (FIG. 20A). Multi-layer stratified structures can be readily seen and are comprised of NPC+ cells marked by SOX 1, SOX2, and PAX6 marking the progenitor zone (FIG. 20A-FIG. 20C). PAX6 expression confirmed the forebrain identity in the regions of interest. Nestin positive cells mark radial glia, key structures for the expansion of the mammalian cortex by differentiating into neurons and intermediate progenitor cells (FIG. 20A and FIG. 20B)

Figure 21A:
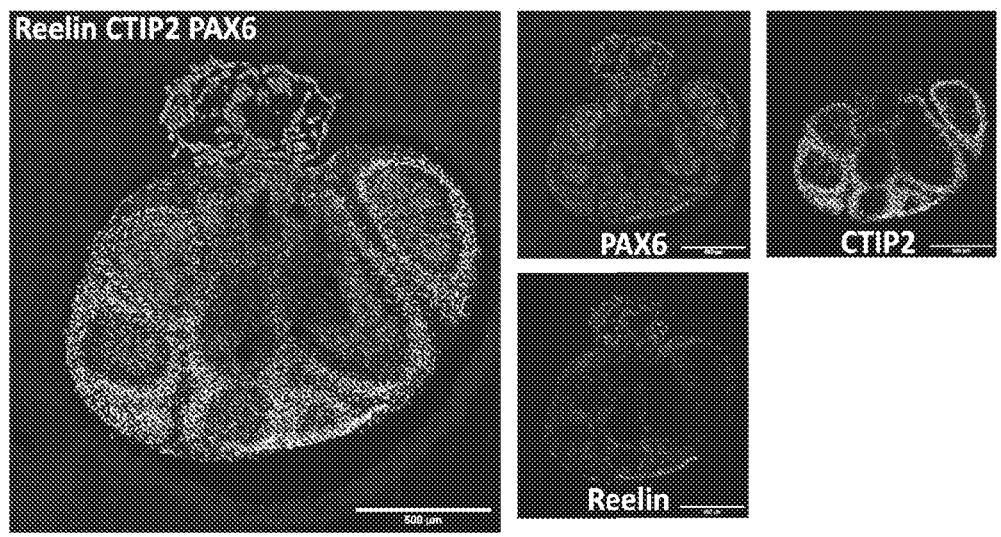
FIG. 21A-FIG. 21C show characterization of cortical layers present after 60 days in culture.

Pre-plate formation was confirmed by the presence of T-box brain (TBR) 1+ cells (FIG. 20B and FIG. 20C). This marker also identifies cells localized to the early-born layer VI of the cortex. TBR1+ neurons are vital for guiding the subsequent neuronal migrations. Radial organization can be seen by Microtubule-associated protein (MAP) 2, a neuronal marker for dendritic outgrowth and branching (FIG. 20C). Cajal-Retzius cells, a cell population crucial to the generation of the cortical plate architecture, is present by Reelin+ neurons located along the organoid surface (FIG. 21A). These early born cells localize to the marginal zone of the cortex (layer I) and contribute to the formation of the inside-out layering of the neurons in the neocortex.

Figure 21B:
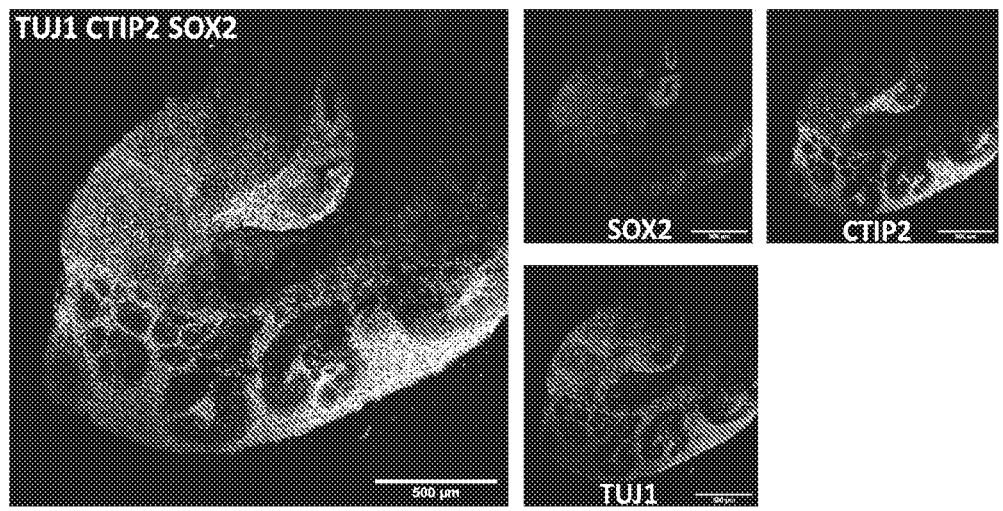
Figure 21C:
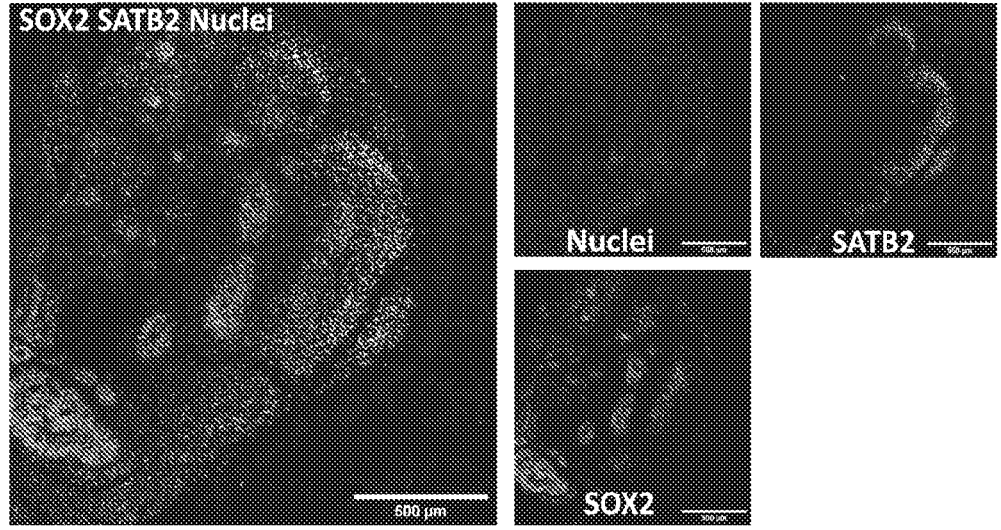

At day 60, early-born neurons from layer V were positive for CTIP2 (also known as B-cell lymphoma/leukemia 11B, BCL11B) (FIG. 21A and FIG. 21B). Furthermore, late-born neurons from the superficial layers (layer IV) can be seen as Special AT-rich sequence-binding protein (SATB) 2+ cells (FIG. 21C). Interestingly, these markers show a clear separation from the neural progenitor zone, indicating a spatial separation of the different neuronal lineages, as well as the recapitulation of the cortical architecture observed in other brain organoid protocols.

Figure 22A:
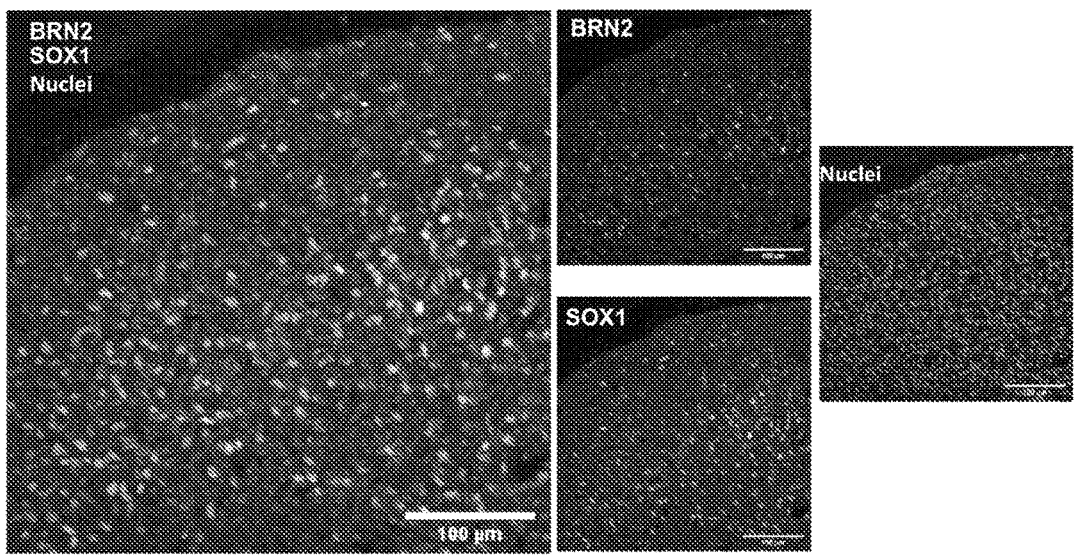
FIG. 22A and FIG. 22B show long term culture of brain organoids allows upper layer specification. Sample images of immunostaining for superficial layer neuron markers (FIG. 22A) BRN2 and (FIG. 22B) CUX1 in cerebral organoids at day 150. Immunostainings were repeated on four brain organoids from one independent experiment. Scale bars: 100 µm.
Figure 22B:
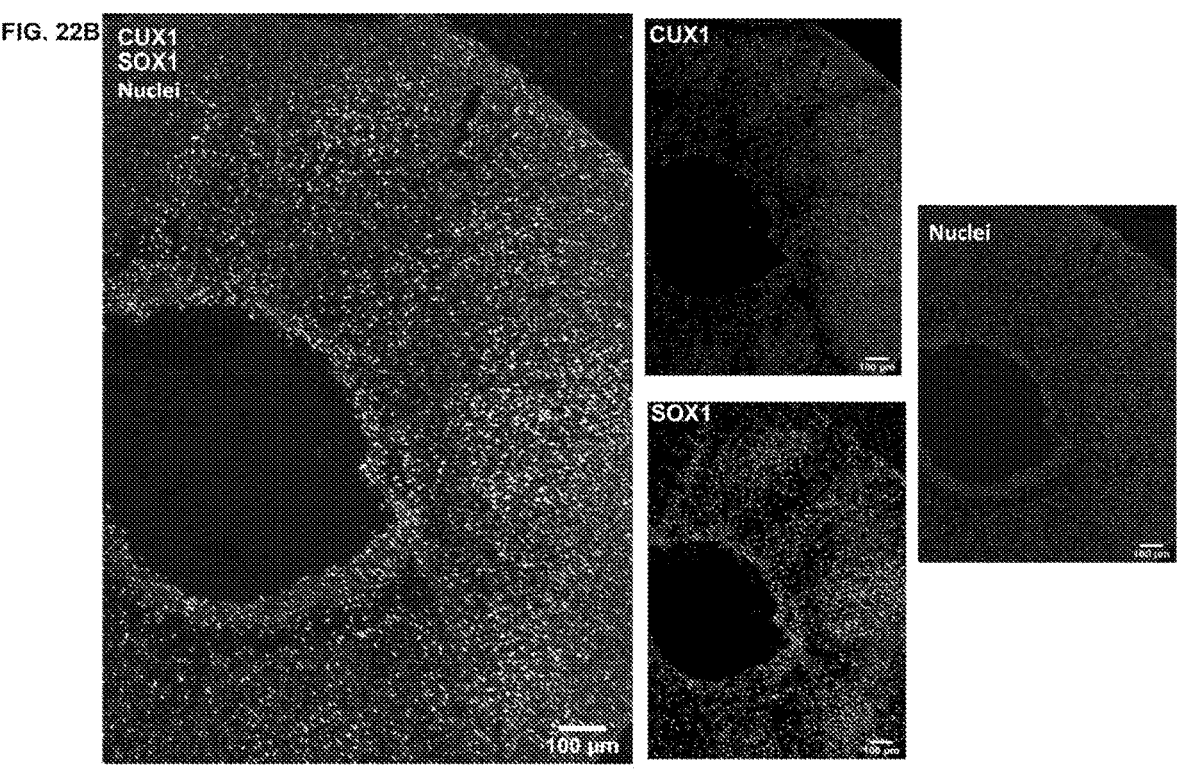

Neurons expressing layer II/III markers Cut Like Homeobox (CUX) 1 and BRN2 are present by day 150 (FIG. 22A and FIG. 22B). Presence of these late born neurons underlie the capacity of the organoid system to recapitulate the cytoarchitecture of the developing cortex.

Figure 23A:
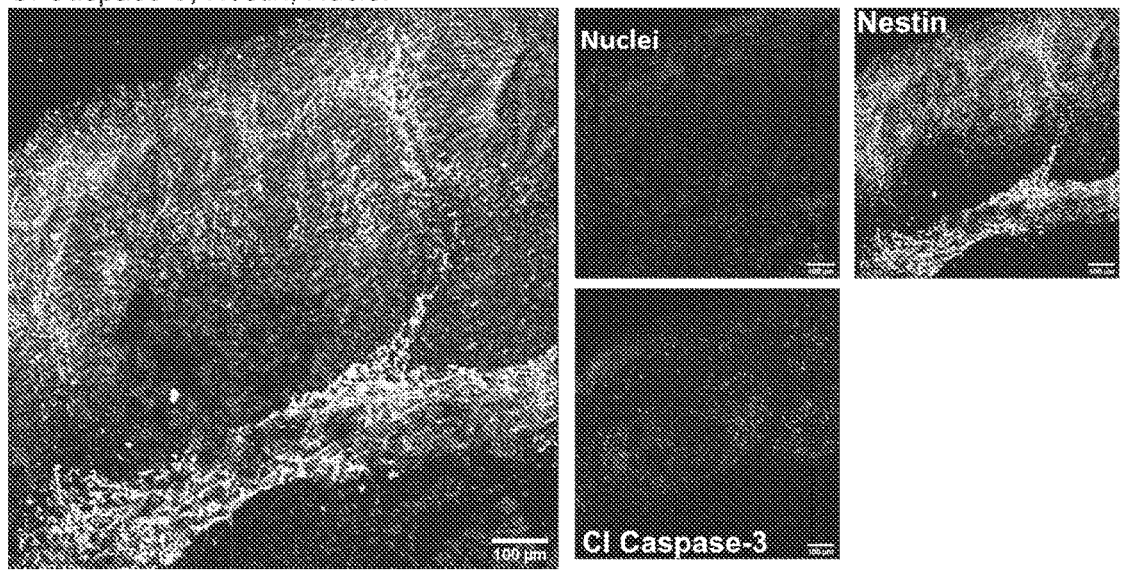
FIG. 23A and FIG. 23B show immunostaining for apoptosis marker Caspase 3.
Figure 23B:
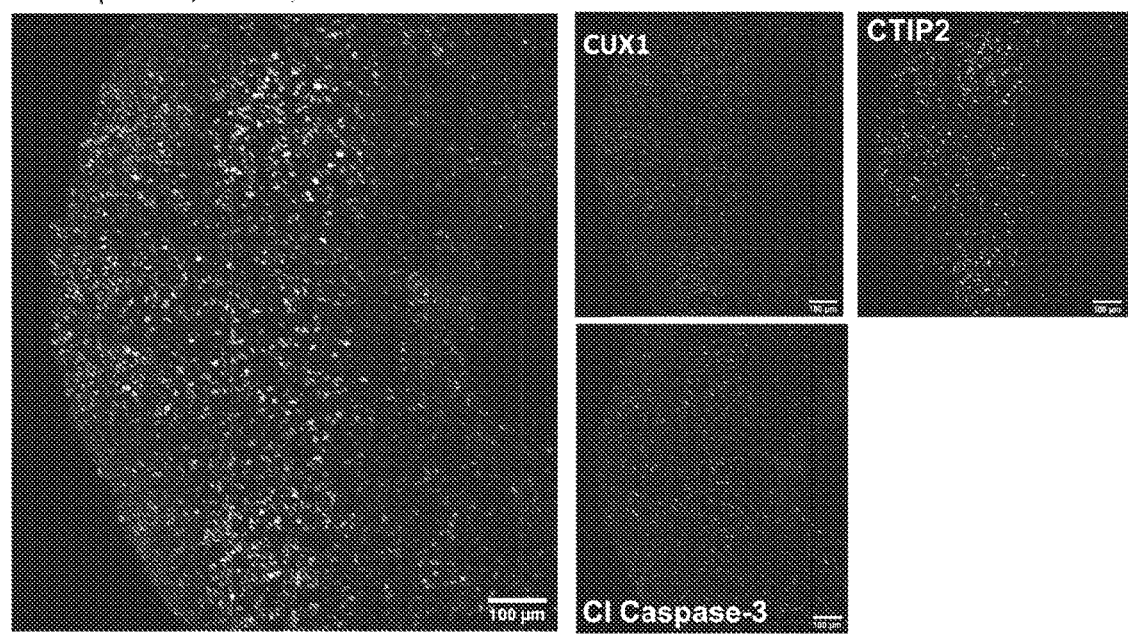

Finally, an analysis of the presence of the apoptosis marker cleaved Caspase 3 (ClC3) was performed. At day 60 and day 150, the presence of apoptosis is evident but the integrity of the cortical structures is maintained (FIG. 23A and FIG. 23B). Apoptosis is a key process during brain formation, controlling cellularity in the developing brain. Work in human, mouse, and rat brain samples shows high incidence of cell death during the development of the neocortex. As the overall architecture of the organoids was maintained, the observed cell death may be the result of the normal elimination of cells that takes place in the developing brain. Additional details may be found in Alejandra I. Romero-Morales, Brian J. O'Grady, Kylie M. Balotin, Leon M. Bellan, Ethan S. Lippmann, Vivian Gama, "Spin∞: an updated miniaturized spinning bioreactor design for the generation of human cerebral organoids from pluripotent stem cells," HardwareX, Volume 6, October 2019, the entire contents of which are hereby incorporated by reference.

These experimental data show that organoids cultured with an exemplary bioreactor system have the growth capacity and laminar organization previously reported in the literature. Brain organoids grow above 3 mm in diameter. Immunohistochemistry analysis shows a distinct neural progenitor zone as well as positive markers for all cortical layers. Human NPC markers, as well as deep cortical and pan-neuronal markers can be identified in a structured manner and in the expected stages. Evaluation of the apoptotic marker ClC3 shows cell death in the core of the organoid as expected with no major compromise of the organoid integrity.

Experimental exemplary bioreactor systems demonstrated one or more of the following. Brain organoids were grown over 150 days, and successfully cultured over 200 days, without the need to change motors, which demonstrates the increased motor life span of exemplary bioreactor systems under high temperature and humidity conditions. No contamination was detected even after long-term culture, which we hypothesize is due in part to the ability to autoclave the majority of bioreactor system components after assembly.

The foregoing detailed description and accompanying examples are merely illustrative and are not to be taken as limitations upon the scope of the disclosure. Various changes and modifications to the disclosed embodiments will be apparent to those skilled in the art. Such changes and modifications, including without limitation those relating to the chemical structures, substituents, derivatives, intermediates, syntheses, compositions, formulations, or methods of use, may be made without departing from the spirit and scope of the disclosure.

What is claimed is:

1. A bioreactor system, comprising:
a first frame and a second frame connected to the first frame,
the first frame defining a well plate inset and standoff insets for a first set of metal standoffs;
a well plate positioned within the well plate inset, the well plate defining a plurality of wells;
the second frame defining a plurality of mounts;
the second frame defining a plurality of insets for a second set of metal standoffs,
wherein a polymer collar is coupled to each of the plurality of mounts;
wherein a gear is positioned in each of the plurality of mounts;
wherein each of the plurality of gears is in communication with at least one adjacent gear;
wherein a paddle is coupled to each of the plurality of gears;
wherein each paddle is positioned within one of the plurality of wells;
a motor plate supported by and connected to the first set of metal standoffs and the second set of metal standoffs,
wherein the first set of metal standoffs extend between the first frame and the motor plate,
wherein the second set of metal standoffs extend between the second frame and the motor plate, and
wherein a length of the first set of metal standoffs is greater than a length of the second set of metal standoffs;
a motor mounted on the motor plate, the motor being operatively connected to one of the plurality of gears; and a controller in communication with the motor, the controller programmed to control a speed of the motor.

2. The bioreactor system according to claim 1, wherein the motor plate is arranged parallel to the second frame.

3. The bioreactor system according to claim 2, wherein the first set of metal standoffs and the second set of metal standoffs are stainless steel.

4. The bioreactor system according to claim 1, wherein the well plate defines 12 wells; and
wherein the second frame defines 12 mounts.

5. The bioreactor system according to claim 1, wherein the motor is connected to the gear in a second row and a second column of the mounts defined by the second frame.

6. The bioreactor system according to claim 1, wherein the first frame and the second frame are made from acrylic additive manufacturing resin.

7. The bioreactor system according to claim 6, wherein the acrylic additive manufacturing resin includes polyetherimide.

8. The bioreactor system according to claim 1, wherein each of the first frame, the second frame, the motor plate, and the motor include a parylene coating.

9. The bioreactor system according to claim 1, wherein the polymer collar is polytetrafluoroethylene (PTFE).

10. The bioreactor system according to claim 1, wherein the controller is programmed to operate the motor at a speed between 10 RPM and 100 RPM.

11. The bioreactor system according to claim 1, further comprising an incubation device configured to control a temperature and a humidity during operation of the bioreactor system.

12. A method of using a bioreactor system according to claim 1, the method comprising:
adding media to each of the plurality of wells;
initiating motor activation at a predetermined rotational speed:
adjusting a temperature of an environment surrounding the bioreactor system to a predetermined temperature range;
adjusting a humidity of the environment to a predetermined humidity range;
continuing motor activation for at least 60 days;
ceasing motor activation after at least 60 days; and
removing the well plate from the first frame.

13. The method according to claim 12, wherein the predetermined rotational speed is between 10 RPMs and 100 RPMs.

14. The method according to claim 13, wherein the predetermined temperature range is between 40° C. and 70° C.

15. The method according to claim 14, wherein the predetermined humidity range is between 40% and 90%.

16. A bioreactor system, comprising:
a first frame and a second frame connected to the first frame,
the first frame defining a well plate inset and standoff insets for a first set of metal standoffs;
a well plate positioned within the well plate inset, the well plate defining a plurality of wells;
the second frame defining a plurality of mounts;
the second frame defining a plurality of insets for a second set of metal standoffs,
wherein a polymer collar is coupled to each of the plurality of mounts;
wherein a gear is positioned in each of the plurality of mounts;
wherein each of the plurality of gears is in communication with at least one adjacent gear;
wherein a paddle is coupled to each of the plurality of gears, each paddle being located on an opposite side of the second frame from the plurality of gears;
wherein each paddle is positioned within one of the plurality of wells;
a motor plate supported by and connected to the first set of metal standoffs and the second set of metal standoffs,
wherein each of the first frame, second frame, and motor plate are arranged parallel to each other,
wherein the first set of metal standoffs extend between the first frame and the motor plate,
wherein the second set of metal standoffs extend between the second frame and the motor plate, and
wherein a length of the first set of metal standoffs is greater than a length of the second set of metal standoffs;
a motor mounted on the motor plate, the motor being operatively connected to one of the plurality of gears; and
a controller in communication with the motor, the controller programmed to control a speed of the motor.

17. The bioreactor system according to claim 16, wherein the first frame and the second frame are made from acrylic additive manufacturing resin;
wherein each of the first frame, the second frame, the motor plate, and the motor include a parylene coating; and
wherein the polymer collar is polytetrafluoroethylene (PTFE).

18. The bioreactor system according to claim 17, wherein the controller is programmed to operate the motor at a speed between 10 RPM and 100 RPM.

19. The bioreactor system according to claim 16, wherein the first set of metal standoffs and the second set of metal standoffs are stainless steel;
wherein the well plate defines 12 wells;
wherein the second frame defines 12 mounts; and
wherein the motor is connected to the gear in a second row and a second column of the mounts defined by the second frame.

* * * * *